(12) United States Patent
Hartmann et al.

(10) Patent No.: US 10,174,326 B2
(45) Date of Patent: Jan. 8, 2019

(54) TLR7 LIGAND AND USES THEREOF

(75) Inventors: Gunther Hartmann, Bonn (DE); Winfried Barchet, Bonn (DE); Vera Wimmenauer, Buenos Aires (AR)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 82 days.

(21) Appl. No.: 13/130,630

(22) PCT Filed: Mar. 17, 2010

(86) PCT No.: PCT/EP2010/001686
§ 371 (c)(1),
(2), (4) Date: Jun. 22, 2011

(87) PCT Pub. No.: WO2010/105819
PCT Pub. Date: Sep. 23, 2010

(65) Prior Publication Data
US 2011/0250175 A1 Oct. 13, 2011

(30) Foreign Application Priority Data
Mar. 17, 2009 (EP) .................................. 09003837

(51) Int. Cl.
*C12N 15/117* (2010.01)
(52) U.S. Cl.
CPC ........ *C12N 15/117* (2013.01); *C12N 2310/17* (2013.01)
(58) Field of Classification Search
None
See application file for complete search history.

(56) References Cited

U.S. PATENT DOCUMENTS

2004/0073380 A1* 4/2004 Puglisi ........................... 702/25
2006/0172966 A1* 8/2006 Lipford et al. ................. 514/44

FOREIGN PATENT DOCUMENTS

| WO | WO 2003/086280 A2 | 10/2003 |
| WO | WO 2007/062107 A2 | 5/2007 |
| WO | WO 2008/017473 A2 | 2/2008 |
| WO | WO 2008/139262 A1 | 11/2008 |
| WO | WO 2009/100502 A1 | 8/2009 |

OTHER PUBLICATIONS

Sun et al., Nucl. Acids Res., 2008, 36: 1654-1664.*
Kaiser, 2007.*
Dallas et al., Current Biology, 1997, 5: 1639-1653.*
Agris et al., J. Mol. Biol., 2007, 366: 1-13.*
Blanco et al., Science, 2001, 294: 1540-1543.*
Monteleone et al., Eur. J. Immunol., 2001, 31: 2247-2255.*
Kovarik et al., Transplantation, 1988, 45: 402-405; Abstract.*
Stifter et al., J. Immunol., 2015, 194: 2455-2465.*
Teijaro et al., Current Opinion in Virology, 2016, 16: 31-40.*
Davidson et al., J. Interferon & Cytokine Res., 2015, 35: 252-264.*
Mandl et al., Nature Medicine, 2008, 14: 1077-1087.*
Gondai et al., "Short-hairpin RNAs synthesized by T7 phage polymerase do not induce interferon," *Nucleic Acids Research*, 36(3): E18, pp. 1-8 (2008).
European Patent Office, International Search Report in International Patent Application No. PCT/EP2010/001686 (dated Jul. 7, 2010).
European Patent Office, Search Report in European Patent Application No. EP 10709804.8 (dated Nov. 13, 2013).
Alexopoulou et al., "Recognition of double-stranded RNA and activation of NF-κB by Toll-like receptor 3," *Nature*, 413: 732-738 (Oct. 18, 2001).
Barchet et al., "Dendritic cells respond to influenza virus through TLR7- and PKR-independent pathways," *European Journal of Immunology*, 35(1): 236-242 (Jan. 2005).
Barrat et al., "Nucleic acids of mammalian origin can act as endogenous ligands for Toll-like receptors and may promote systemic lupus erythematosus," *Journal of Experimental Medicine*, 202(8): 1131-1139 (Oct. 17, 2005).
Bekeredjian-Ding et al., "Plasmacytoid Dendritic Cells Control TLR7 Sensitivity of Naïve B Cells via Type I IFN," *Journal of Immunology*, 174: 4043-4050 (2005).
Bekeredjian-Ding et al., "T Cell-Independent, TLR-Induced IL-12p70 Production in Primary Human Monocytes," *Journal of Immunology*, 176: 7438-7446 (2006).
Chuang et al., "Cloning and characterization of a sub-family of human toll-like receptors: hTLR7, hTLR8 and hTLR9," *Eur. Cytokine Netw.*, 11(3): 372-378 (Sep. 2000).
Diebold et al., "Viral infection switches non-plasmacytoid dendritic cells into high interferon producers," *Nature*, 424: 324-328 (Jul. 17, 2003).
Diebold et al., "Innate Antiviral Responses by Means of TLR7-Mediated Recognition of Single-Stranded RNA," *Science*, 303: 1529-1531 (Mar. 5, 2004).
Diebold et al., "Nucleic acid agonists for Toll-like receptor 7 are defined by the presence of uridine ribonucleotides," *European Journal of Immunology*, 36: 3256-3267 (2006).
Eberle et al., "Modifications in Small Interfering RNA That Separate Immunostimulation from RNA Interference," *Journal of Immunology*, 180: 3229-3237 (2008).
Forsbach et al., Identification of RNA Sequence Motifs Stimulating Sequence-Specific TLR8-Dependent Immune Responses, *Journal of Immunology*, 180: 3729-3738 (2008).
Gitlin et al., "Essential role of mda-5 in type I IFN responses to polyriboinosinic: polyribocytidylic acid and encephalomyocarditis picornavirus," *Proc. Natl. Acad. Sci. USA*, 103(22): 8459-8464 (May 30, 2006).
Gorden et al., "Synthetic TLR Agonists Reveal Functional Differences between Human TLR7 and TLR8," *Journal of Immunology*, 174: 1259-1268 (2005).

(Continued)

*Primary Examiner* — Ileana Popa
(74) *Attorney, Agent, or Firm* — Leydig, Voit & Mayer, Ltd.

(57) ABSTRACT

The present invention provides a TLR7 ligand and its use in therapeutic applications. Specifically, the present application provides a RNA oligonucleotide comprising a G:U wobble base pair in the context of a fully double-stranded structure and its use in treating disease such as viral infections, immune disorders and cancer.

15 Claims, 14 Drawing Sheets
Specification includes a Sequence Listing.

(56) References Cited

OTHER PUBLICATIONS

Hattermann et al., "The Toll-like receptor 7/8-ligand resiquimod (R-848) primes human neutrophils for leukotriene $B_4$, prostaglandin $E_2$ and platelet-activating factor biosynthesis," *FASEB J.*, 21(7): 1575-1585 (May 2007).
Heil et al., "The Toll-like receptor 7 (TLR7)—specific stimulus loxoribine uncovers a strong relationship within the TLR7, 8 and 9 subfamily," *European Journal of Immunology*, 33(11): 2987-2997 (Nov. 2003).
Heil et al., "Species-Specific Recognition of Single-Stranded RNA via Toll-like Receptor 7 and 8," *Science*, 303: 1526-1529 (Mar. 5, 2004).
Hemmi et al., "A Toll-like receptor recognizes bacterial DNA," *Nature*, 408: 740-745 (Dec. 7, 2000).
Hornung et al., "Quantitative Expression of Toll-Like Receptor 1-10 mRNA in Cellular Subsets of Human Peripheral Blood Mononuclear Cells and Sensitivity to CpG Oligodeoxynucleotides," *Journal of Immunology*, 168: 4531-4537 (2002).
Hornung et al., "Sequence-specific potent induction of IFN-α by short interfering RNA in plasmacytoid dendritic cells through TLR7," *Nature Medicine*, 11(3): 263-270 (Mar. 2005).
Judge et al., "Sequence-dependent stimulation of the mammalian innate immune response by synthetic siRNA," *Nature Biotechnology*, 23(4): 457-462 (Apr. 2005).
Jurk et al., "Human TLR7 or TLR8 independently confer responsiveness to the antiviral compound R-848," *Nature Immunology*, 3(6): 499 (Jun. 2002).
Kadowaki et al., "Subsets of Human Dendritic Cell Precursors Express Different Toll-like Receptors and Respond to Different Microbial Antigens," *Journal of Experimental Medicine*, 194(6): 863-869 (Sep. 17, 2001).
Krieg et al., "Toll-like receptors 7, 8, and 9: linking innate immunity to autoimmunity," *Immunological Reviews*, 220: 251-269 (2007).
Krug et al., "Herpes simplex virus type 1 activates murine natural interferon-producing cells through toll-like receptor 9," *Blood*, 103(4): 1433-1437 (Feb. 15, 2004).
Lau et al., "RNA-associated autoantigens activate B cells by combined B cell antigen receptor/Toll-like receptor 7 engagement," *Journal of Experimental Medicine*, 202(9): 1171-1177 (Nov. 7, 2005).
Lee et al., "Molecular basis for the immunostimulatory activity of guanine nucleoside analogs: Activation of Toll-like receptor 7," *Proc. Natl. Acad. Sci., USA*, 100(11): 6646-6651 (May 27, 2003).
Lund et al., "Toll-like Receptor 9-mediated Recognition of Herpes Simplex Virus-2 by Plasmacytoid Dendritic Cells," *Journal of Experimental Medicine*, 198(3): 513-520 (Aug. 4, 2003).
Lund et al., "Recognition of single-stranded RNA viruses by Toll-like receptor 7," *Proc. Natl. Acad. Sci. USA*, 101(15): 5598-5603 (Apr. 13, 2004).
Ma et al., "Toll-like receptor 8 functions as a negative regulator of neurite outgrowth and inducer of neuronal apoptosis," *Journal of Cell Biology*, 175(2): 209-215 (Oct. 23, 2006).
Masquida et al., "On the wobble GoU and related pairs," *RNA*, 6: 9-15 (2000).
Mathews et al., "Prediction of RNA secondary structure by free energy minimization," *Current Opinion in Structural Biology*, 16(3): 270-278 (Jun. 2006).
Palecanda et al., "Receptors for Unopsonized Particles: The Role of Alveolar Macrophage Scavenger Receptors," *Current Molecular Medicine*, 1(5): 589-595 (2001).
Scheel et al., "Toll-like receptor-dependent activation of several human blood cell types by protamine-condensed mRNA," *European Journal of Immunology*, 35(5): 1557-1566 (May 2005).
Sioud, "Single-stranded small interfering RNA are more immunostimulatory than their double-stranded counterparts: A central role for 2'-hydroxyl uridines in immune responses," *European Journal of Immunology*, 36: 1222-1230 (2006).

Uematsu et al., "Toll-Like Receptors (TLRs) and Their Ligands," *Toll-Like Receptors and Innate Immunity. Handbook of Experimental Pharmacology*, 183 (S. Bauer ed.), 1-20 (Spring-Verlag, Berlin, 2008).
Varani et al., "The G•U wobble base pair. A fundamental building block of RNA structure crucial to RNA function in diverse biological systems," *EMBO Reports*, 1(1): 18-23 (2000).
Wagstaff et al., "Topical Imiquimod: A Review of its Use in the Management of Anogenital Warts, Actinic Keratoses, Basal Cell Carcinoma and Other Skin Lesions," *Drugs*, 67(15): 2187-2210 (2007).
Xu et al., "The electrostatic characteristics of G • U wobble base pairs," *Nucleic Acids Research*, 35(11): 3836-3847 (2007).
Kaiser, "Toll-Like Receptors Recognizing Viral Double-Stranded RNA," (Aug. 26, 2014) [https://web.archive.org/web/20120623214045/http://faculty.ccbcmd.edu/courses/bio141/lecguide/unit4/innate/tlrviralanim.html].
Zhang et al., "Structural Analysis Reveals that Toll-like Receptor 7 is a Dual Receptor for Guanosine and Single-Stranded RNA," *Immunity*, vol. 45: pp. 1-12 (Oct. 18, 2016).
Ambach et al., "Imiquimod, a Toll-like receptor-7 agonist, induces perforin in cytotoxic T lymphocytes in vitro", *Mol Immunol.*, 40(18): 1307-14., Erratum in: *Mol Immunol.*, 41(12): 1253. (2004).
Asahi-Ozaki et al., "Intranasal administration of adjuvant-combined recombinant influenza virus HA vaccine protects mice from the lethal H5NI virus infection", *Microbes Infect.*, 8(12-13):2706-14. (2006).
Hamm et al., "Immunostimulatory RNA is a potent inducer of antigen-specific cytotoxic and humoral immune response in vivo", *Int Immunol.*, 19(3): 297-304. (2007).
Hart et al., "TLR7/8-mediated activation of human NK cells results in accessory cell-dependent IFNgamma production", *J Immunol.*, 175(3) :1636-42. (2005).
Johansen et al., "Toll-like receptor ligands as adjuvants in allergen-specific immunotherapy", *Clin Exp Allergy.*, 35(12) :1591-8. (2005).
Johnston et al., "TLR7 imidazoquinoline ligand 3M-019 is a potent adjuvant for pure protein prototype vaccines", *Cancer Immunol Immunother.*, 56(8): 1133-41. (2007).
Loré et al., "Toll-like receptor ligands modulate dendritic cells to augment cytomegalovirus- and HIV-1-specific T cell responses", *J Immunol.*, 171(8): 4320-8. (2003).
Ma et al., "Additive effects of CpG ODN and R-848 as adjuvants on augmenting immune responses to HBsAg vaccination", *Biochem Biophys Res Commun.*, 361(2): 537-42. (2007).
Miller et al., "The antiviral activity of Toll-like receptor 7 and 7/8 agonists", *Drug News Perspect.* 21(2): 69-87. (2008).
Othoro et al., "Enhanced immunogenicity of Plasmodium falciparum peptide vaccines using a topical adjuvant containing a potent synthetic Toll-like receptor 7 agonist, imiquimod", *Infect Immun.* 77(2): 739-48. (2009).
Weeratna et al., "TLR agonists as vaccine adjuvants: comparison of CpG ODN and Resiquimod (R-848)", *Vaccine*, 23(45): 5263-70. (2005).
Wille-Reece et al., "Immunization with HIV-1 Gag protein conjugated to a TLR7/8 agonist results in the generation of HIV-1 Gag-specific Th1 and CDS+ T cell responses", *J. Immunol.*, 174(12):7676-83. (2005).
Wille-Reece et al., "Toll-like receptor agonists influence the magnitude and quality of memory T cell responses after prime-boost immunization in nonhuman primates", *J Exp Med.*, 203(5) :1249-58. (2006).
Zhang et al., "Immunization with a Toll-like receptor 7 and/or 8 agonist vaccine adjuvant increases protective immunity against Leishmania major in BALB/c mice", *Infect Immun.*, 76(8): 3777-83. (2008).
European Patent Office, Extended European Search Report issued in European Application No. 17168762.7 (dated Dec. 1, 2017) 10 pp.
Smits et al., "The Use of TLR7 and TLR8 Ligands for the Enhancement of Cancer Immunotherapy", *The Oncologist: Clinical Pharmacology*, 13: 859-875 (2008).

\* cited by examiner

… (1) …

SEQUENCE LISTING

```
<160> NUMBER OF SEQ ID NOS: 38

<210> SEQ ID NO 1
<211> LENGTH: 8
<212> TYPE: RNA
<213> ORGANISM: Artificial Sequence
<220> FEATURE:
<223> OTHER INFORMATION: synthetic

<400> SEQUENCE: 1 aaaaaaaa                                                                  8

<210> SEQ ID NO 2
<211> LENGTH: 8
<212> TYPE: RNA
<213> ORGANISM: Artificial Sequence
<220> FEATURE:
<223> OTHER INFORMATION: synthetic

<400> SEQUENCE: 2 cccccccc                                                                  8

<210> SEQ ID NO 3
<211> LENGTH: 8
<212> TYPE: RNA
<213> ORGANISM: Artificial Sequence
<220> FEATURE:
<223> OTHER INFORMATION: synthetic

<400> SEQUENCE: 3 gggggggg                                                                  8

<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4
gggggggggg gggggggggg g                                                  21

<210> SEQ ID NO 5
<211> LENGTH: 21
<212> TYPE: RNA
<213> ORGANISM: Artificial Sequence
<220> FEATURE:
<223> OTHER INFORMATION: synthetic

<400> SEQUENCE: 5
uuuuuuuuuu uuuuuuuuuu u                                                  21

<210> SEQ ID NO 6
<211> LENGTH: 21
<212> TYPE: RNA
<213> ORGANISM: Artificial Sequence
```

```
<220> FEATURE:
<223> OTHER INFORMATION: synthetic
<220> FEATURE:
<221> NAME/KEY: misc_binding
<222> LOCATION: (1)...(21)
<223> OTHER INFORMATION: phosphothioate bonds

<400> SEQUENCE: 6
uuuuuuuuuu uuuuuuuuuu u                                        21

<210> SEQ ID NO 7
<211> LENGTH: 21
<212> TYPE: RNA
<213> ORGANISM: Artificial Sequence
<220> FEATURE:
<223> OTHER INFORMATION: synthetic

<400> SEQUENCE: 7
aaaaaaaaaa aaaaaaaaaa a                                        21

<210> SEQ ID NO 8
<211> LENGTH: 21
<212> TYPE: RNA
<213> ORGANISM: Artificial Sequence
<220> FEATURE:
<223> OTHER INFORMATION: synthetic

<400> SEQUENCE: 8
cccccccccc cccccccccc c                                        21

<210> SEQ ID NO 9
<211> LENGTH: 6
<212> TYPE: RNA
<213> ORGANISM: Artificial Sequence
<220> FEATURE:
<223> OTHER INFORMATION: synthetic

<400> SEQUENCE: 9 cccucc                                                          6

<210> SEQ ID NO 10
<211> LENGTH: 7
<212> TYPE: RNA
<213> ORGANISM: Artificial Sequence
<220> FEATURE:
<223> OTHER INFORMATION: synthetic

<400> SEQUENCE: 10 cccuccc                                                         7

<210> SEQ ID NO 11
<211> LENGTH: 8
<212> TYPE: RNA
<213> ORGANISM: Artificial Sequence
<220> FEATURE:
<223> OTHER INFORMATION: synthetic

<400> SEQUENCE: 11 ccccuccc                                                        8

<210> SEQ ID NO 12
<211> LENGTH: 10
<212> TYPE: RNA
<213> ORGANISM: Artificial Sequence
<220> FEATURE:
<223> OTHER INFORMATION: synthetic
```

```
<400> SEQUENCE: 12
cccccuccc                                                          10

<210> SEQ ID NO 13
<211> LENGTH: 12
<212> TYPE: RNA
<213> ORGANISM: Artificial Sequence
<220> FEATURE:
<223> OTHER INFORMATION: synthetic

<400> SEQUENCE: 13 cccccucc cc                                                        12

<210> SEQ ID NO 14
<211> LENGTH: 16
<212> TYPE: RNA
<213> ORGANISM: Artificial Sequence
<220> FEATURE:
<223> OTHER INFORMATION: synthetic

<400> SEQUENCE: 14
ccccccccuc cccccc                                                  16

<210> SEQ ID NO 15
<211> LENGTH: 21
<212> TYPE: RNA
<213> ORGANISM: Artificial Sequence
<220> FEATURE:
<223> OTHER INFORMATION: synthetic

<400> SEQUENCE: 15
cccccccccc uccccccccc c                                            21

<210> SEQ ID NO 16
<211> LENGTH: 8
<212> TYPE: RNA
<213> ORGANISM: Artificial Sequence
<220> FEATURE:
<223> OTHER INFORMATION: synthetic

<400> SEQUENCE: 16 aaaagaaa                                                            8

<210> SEQ ID NO 17
<211> LENGTH: 12
<212> TYPE: RNA
<213> ORGANISM: Artificial Sequence
<220> FEATURE:
<223> OTHER INFORMATION: synthetic

<400> SEQUENCE: 17
aaaaaagaaa aa                                                      12

<210> SEQ ID NO 18
<211> LENGTH: 14
<212> TYPE: RNA
<213> ORGANISM: Artificial Sequence
<220> FEATURE:
<223> OTHER INFORMATION: synthetic

<400> SEQUENCE: 18
aaaaaaagaa aaaa                                                    14
```

```
<210> SEQ ID NO 19
<211> LENGTH: 16
<212> TYPE: RNA
<213> ORGANISM: Artificial Sequence
<220> FEATURE:
<223> OTHER INFORMATION: synthetic

<400> SEQUENCE: 19
aaaaaaaaga aaaaaa                                                         16

<210> SEQ ID NO 20
<211> LENGTH: 21
<212> TYPE: RNA
<213> ORGANISM: Artificial Sequence
<220> FEATURE:
<223> OTHER INFORMATION: synthetic

<400> SEQUENCE: 20
aaaaaaaaaa gaaaaaaaaa a                                                   21

<210> SEQ ID NO 21
<211> LENGTH: 21
<212> TYPE: RNA
<213> ORGANISM: Artificial Sequence
<220> FEATURE:
<223> OTHER INFORMATION: synthetic

<400> SEQUENCE: 21
aaaaagaaaa aaaaagaaa a                                                    21

<210> SEQ ID NO 22
<211> LENGTH: 19
<212> TYPE: RNA
<213> ORGANISM: Artificial Sequence
<220> FEATURE:
<223> OTHER INFORMATION: synthetic

<400> SEQUENCE: 22
agcuuaaccu guccuucaa                                                      19

<210> SEQ ID NO 23
<211> LENGTH: 19
<212> TYPE: RNA
<213> ORGANISM: Artificial Sequence
<220> FEATURE:
<223> OTHER INFORMATION: synthetic

<400> SEQUENCE: 23
ggcauucuua uucuuacgg                                                      19

<210> SEQ ID NO 24
<211> LENGTH: 19
<212> TYPE: RNA
<213> ORGANISM: Artificial Sequence
<220> FEATURE:
<223> OTHER INFORMATION: synthetic

<400> SEQUENCE: 24
ggcauucuua uucuuacgg                                                      19

<210> SEQ ID NO 25
<211> LENGTH: 21
<212> TYPE: RNA
<213> ORGANISM: Artificial Sequence
<220> FEATURE:
<223> OTHER INFORMATION: synthetic
```

<400> SEQUENCE: 25
cccuccccgg ggggggggggg g                                    21

<210> SEQ ID NO 26
<211> LENGTH: 21
<212> TYPE: RNA
<213> ORGANISM: Artificial Sequence
<220> FEATURE:
<223> OTHER INFORMATION: synthetic

<400> SEQUENCE: 26
gggggggggg gggcccuccc c                                     21

<210> SEQ ID NO 27
<211> LENGTH: 21
<212> TYPE: RNA
<213> ORGANISM: Artificial Sequence
<220> FEATURE:
<223> OTHER INFORMATION: synthetic

<400> SEQUENCE: 27
cccuccgggg gggggggggg g                                     21

<210> SEQ ID NO 28
<211> LENGTH: 31
<212> TYPE: RNA
<213> ORGANISM: Artificial Sequence
<220> FEATURE:
<223> OTHER INFORMATION: synthetic

<400> SEQUENCE: 28
cccuccccgg gggggggggg gggggggggg g                          31

<210> SEQ ID NO 29
<211> LENGTH: 21
<212> TYPE: RNA
<213> ORGANISM: Artificial Sequence
<220> FEATURE:
<223> OTHER INFORMATION: synthetic

<400> SEQUENCE: 29
ccccccccgg gggggggugg g                                     21

<210> SEQ ID NO 30
<211> LENGTH: 21
<212> TYPE: RNA
<213> ORGANISM: Artificial Sequence
<220> FEATURE:
<223> OTHER INFORMATION: synthetic

<400> SEQUENCE: 30
cgcgcgcgca gaagcgugcg c                                     21

<210> SEQ ID NO 31
<211> LENGTH: 21
<212> TYPE: RNA
<213> ORGANISM: Artificial Sequence
<220> FEATURE:
<223> OTHER INFORMATION: synthetic

<400> SEQUENCE: 31
cgcgugcgca gaagcgcgcg c                                     21

```
<210> SEQ ID NO 32
<211> LENGTH: 21
<212> TYPE: RNA
<213> ORGANISM: Artificial Sequence
<220> FEATURE:
<223> OTHER INFORMATION: synthetic

<400> SEQUENCE: 32
cggcucggca gaagccgggc c                                              21

<210> SEQ ID NO 33
<211> LENGTH: 21
<212> TYPE: RNA
<213> ORGANISM: Artificial Sequence
<220> FEATURE:
<223> OTHER INFORMATION: synthetic

<400> SEQUENCE: 33
cgccugggca gaagcccggg c                                              21

<210> SEQ ID NO 34
<211> LENGTH: 8
<212> TYPE: RNA
<213> ORGANISM: Artificial Sequence
<220> FEATURE:
<223> OTHER INFORMATION: synthetic
<220> FEATURE:
<223> OTHER INFORMATION: u = uridin

<400> SEQUENCE: 34 ccccuccc                                                              8

<210> SEQ ID NO 35
<211> LENGTH: 8
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)...(5)
<223> OTHER INFORMATION: n = um = 2'-O-Methyluridin

<400> SEQUENCE: 35 ccccnccc                                                              8

<210> SEQ ID NO 36
<211> LENGTH: 8
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)...(5)
<223> OTHER INFORMATION: n = p = pseudouridin

<400> SEQUENCE: 36 ccccnccc                                                              8

<210> SEQ ID NO 37
<211> LENGTH: 20
<212> TYPE: DNA
<213> ORGANISM: Artificial Sequence
<220> FEATURE:
<223> OTHER INFORMATION: synthetic
```

```
<220> FEATURE:
<221> NAME/KEY: misc_binding
<222> LOCATION: (1)...(3)
<223> OTHER INFORMATION: phosphothioate bonds
<220> FEATURE:
<221> NAME/KEY: misc_binding
<222> LOCATION: (15)...(20)
<223> OTHER INFORMATION: phosphothioate bonds

<400> SEQUENCE: 37
gggggacgat cgtcgggggg                                              20

<210> SEQ ID NO 38
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_binding
<222> LOCATION: (1)...(5)
<223> OTHER INFORMATION: phosphothioate bonds
<220> FEATURE:
<221> NAME/KEY: misc_binding
<222> LOCATION: (17)...(21)
<223> OTHER INFORMATION: phosphothioate bonds

<400> SEQUENCE: 38
ggggacgacg tcgtgggggg g                                            21
```

TLR7 LIGAND AND USES THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,434 bytes ASCII (Text) file named "708182 SequenceListing.txt" created May 20, 2011.

FIELD OF THE INVENTION

The present invention relates to the field of immunotherapy. The present invention provides a TLR7 ligand and its use in therapeutic applications. Specifically, the present application provides an RNA oligonucleotide comprising a G:U wobble base pair and its use in treating disease such as viral infections, immune disorders and cancer.

BACKGROUND OF THE INVENTION

The family of Toll like receptors (TLRs) is involved in the detection of most classes of pathogens. TLRs on the cell surface recognize conserved molecules of bacteria fungi and parasites that are "foreign" to the host organism [1]. A structurally closely related subset of TLRs has been shown to contribute to the detection of viruses [2-5]. Viruses derive all their components from the infected host cell and therefore do not contain "foreign" molecules. Detection of viruses instead hinges on the strategic localization of TLRs that recognize viral nucleic acids in endosomes and lysosomes. These cellular compartments are not usually accessed by host nucleic acids, but are traversed by most viruses during their infectious cycles. The endosomal TLRs 3, 7/8 and 9 have been shown to recognize double stranded (ds), single stranded (ss) or short double stranded RNA and DNA, respectively [2,6-8]. In humans, the function to recognize viral ssRNA is shared by TLR7 and TLR8 [7], and the expression pattern of both receptors appears mutually exclusive, and is largely confined to immune cell subsets. Among human PBMC, TLR7 is expressed by plasmacytoid dendritic cells (PDCs) and by B cells, while monocytes and myeloid dendritic cells express TLR8 [9,10]. In contrast, mice deficient in TLR7 were found entirely unable to respond to ssRNA ligands, indicating that mouse TLR8 is either inactive, or has a non-immune function [11,12]. The first defined TLR7/8 ligands were imidazoquinoline derivates and C8 and/or N7 modified analogs of guanosine, small molecules known to induce an antiviral response [11,13-15]. Most of these compounds (e.g. resiquimod R-848, 3M-003) activate both, TLR7 and TLR8. Others, including imiquimod R-837, 3M-001 and loxoribine, are TLR7 selective, and mainly stimulate PDC to produce IFN-α, or preferentially activate TLR8 (3M-002), and induce monocytes to secrete TNF-α and IL-12. The differential cytokine profiles are of relevance for the therapeutic use of these compounds. The first drug of this class is 5% imiquimod cream, which is approved for the topical treatment of genital warts caused by human papillomavirus (HPV), as well as of basal cell carcinoma and actinic keratosis [16]. Recognition of cognate RNA ligands by TLR7/8 has been studied mostly using short synthetic oligoribonucleotides (ORNs) [17-22]. To achieve stimulation, ORN must be formulated in a complex with lipid transfection reagents or polycations to enable delivery to the endosomal compartment [6,7,21,23]. It was noted that ORN lacking uridines were not immunostimulatory, and most ORNs rich in guanosines and uridines were stimulatory for both, TLR7 and TLR8 [7]. Stimulatory sequence motifs were reported [21], however a systematic evaluation of sequence motifs has not been performed. Based on the observation that homopolymeric uridine (pU) and ORNs consisting of 21 uridine repeats show TLR7 ligand activity, it was proposed that bona fide RNA recognition motifs may not exist [18]. However, a recent publication confirmed that some ORN sequences lacking guanosines selectively activate TLR8 [20]. Other studies found that compared to the single stranded ORNs, complementary strands in the siRNA duplex show reduced TLR8 activity [24]. The biological impact of a differential recognition of RNA by TLR7 and TLR8 is unknown, and selective activation of human TLR7 by RNA has so far not been reported. Natural ssRNAs including mRNA and viral RNA do not present as a single strand under physiological conditions but form secondary structures in which the majority of bases are paired in double helical stems to minimize free energy [25]. Besides the standard Watson-Crick base pairing RNA secondary structure additionally contains wobble (i.e. non-canonical) base pairs formed by guanosines and uridines [26]. G·U (guanosine.uridine) base pairs can functionally substitute for Watson-Crick base pairs, as they are nearly isomorphic, and of comparable thermodynamic stability [27]. RNA stem structures containing G·U wobble base pairs are present in virtually all functional RNA classes and are therefore a hallmark of ssRNA secondary structure. Moreover, in a wide range of biological processes, unique structural, chemical and conformational characteristics mark sites containing G·U base pairs for recognition by proteins [27,28].

Here, we examined whether RNA secondary structural elements, in particular those that form G·U wobble base pairs, influence ssRNA recognition. We found that short RNA stems were highly immunostimulatory, and selectively activated TLR7 when they contained at least one G·U wobble base pair. The G·U base pair therefore constitutes the so far unappreciated minimal structural motif sufficient to confer TLR7 agonist activity in single stranded RNA. In addition, we identified the first phosphodiester RNA ligand, which selectively stimulates TLR7 on its own, obviating the need for formulation with transfection reagents such as polycations.

Therefore, there is a need in the art to better understand the mechanism by which TLR7 distinguishes between self and non-self RNA. Specifically, there is a need in the art to provide molecules that are specifically recognized by TLR7 and/or activate TLR7. The provision of such molecules allows for the provision of immunostimulatory nucleic acid molecules, which are useful for the production of type I IFN in vitro and in vivo and for treating various diseases, which can be alleviated or even eradicated by type I IFN, such as viral infections, immune disorders and cancers.

SUMMARY OF THE INVENTION

The present invention relates to a method for preparing a RNA polynucleotide or oligonucleotide (poly/oligonucleotide), which is capable of inducing an immune response, preferably an anti-viral response, more preferably a type I IFN response, comprising the steps of:

(a) identifying a nucleotide sequence which allows for the formation of at least one substantially, preferably fully double-stranded section, wherein the at least one double-stranded section comprises at least one G:U base pair, and wherein the at least one double-stranded section has a stability that is comparable to that of a double-stranded section composed of at least 4, preferably 6 to 11, G:C base pairs and at least one, preferably one G:U, base pair or is comparable to a double-stranded section composed of at least 8, preferably 10 to 21, A:U base pairs and at least one, preferably one G:U, base pair, (b) producing an RNA poly/oligonucleotide having the nucleotide sequence identified in (a), and (c) optionally testing the ability of the RNA produced in step (b) to induce a type I IFN response.

The present invention further relates to a single-stranded or double-stranded RNA poly/oligonucleotide comprising at least one substantially, preferably fully double-stranded section, wherein the at least one double-stranded section comprises at least one G:U base pair, and wherein the at least one double-stranded section has a stability that is comparable to that of a double-stranded section composed of at least 4, preferably 6 to 11, G:C base pairs and at least one, preferably one G:U, base pair or a fully double-stranded section composed of at least 8, preferably 10 to 21, A:U base pairs and at least one, preferably one G:U, base pair, wherein the poly/oligonucleotide is capable of inducing an immune response, preferably an anti-viral response, more preferably a type I IFN response The present invention further relates to single-stranded RNA poly/oligonucleotide comprising at least one substantially, preferably fully double-stranded section, wherein the at least one double-stranded section has a structure defined by the following general formula I:

$$X_nG/UV_mN_oW_mU/GY_n \quad \text{(Formula I)},$$

wherein if $X_n$ is followed by G then $W_m$ is followed U, or if $X_n$ is followed by U then $W_m$ is followed by G (in order to form a wobble base pair), wherein $2 \leq n \leq 12$, $2 \leq m \leq 12$ and $2 \leq o \leq 12$; X defines any base that forms Watson-Crick base pairs with corresponding bases in Y; V defines any base that forms Watson-Crick base pairs with corresponding bases in W in an RNA stem structure; N is any base in a loop; and wherein the total length of the RNA defined by Formula I is preferably 15 to 45 bases.

In a further embodiment, the RNA poly/oligonucleotides of the invention is a single-stranded RNA poly/oligonucleotide comprising at least one substantially, preferably fully double-stranded section wherein the one strand or a portion of a strand that forms the at least one double-stranded section are composed of two RNA-strands having a structure defined by the following general formulas II and III, $$5'X_nG/UV_m3' \quad \text{(Formula II)}$$

$$5'_oW_mU/GY_n3' \quad \text{(Formula III)},$$

wherein G/U and U/G are selected that a wobble base pair forms, $2 \leq n \leq 12$, $2 \leq m \leq 12$ and $2 \leq o \leq 12$; X defines any base that forms a Watson-Crick base pair with corresponding bases in Y; V defines any base that forms a Watson-Crick base pair with corresponding bases in W in an RNA stem structure; N is any base in a loop; and wherein the total length of the RNA strands defined by Formula II and III is preferably 5 to 45 bases. Preferably, X represents Gs or Cs that form Watson-Crick base pairs with corresponding G and C bases in Y, and V represents Gs or Cs that form Watson-Crick base pairs with corresponding bases in W.

In one embodiment of the invention, the one strand or a portion of a strand that forms the at least one substantially, preferably fully double-stranded section of the herein defined RNA poly/oligonucleotide contains n base pairs and preferably consists of p G:U and q G:C basepairs, wherein p is an integer less than or equal to n, wherein q is an integer less than or equal to n−1, and wherein p+q=n and n is an integer of at least 5, preferably 6-15.

In a further embodiment of the invention, the one strand or a portion of a strand that forms the at least one substantially, preferably fully double-stranded section of the herein defined RNA poly/oligonucleotide contains n base pairs and preferably consists of p G:U and q A:U, wherein p is an integer less than or equal to n, wherein q is an integer less than or equal to n−1, and wherein p+q=n and n is an integer of at least 9, preferably 12-26.

In a further embodiment, the poly/oligonucleotide of the invention is fully or partially double-stranded, whereby one strand in the double-strand contains, preferably consists of, n G's, and the other strand in the double-strand contains, preferably consists of, p U's and q C's, wherein n, p and q are integers greater than zero, wherein p+q=m, wherein m is an integer up to 25, preferably equal to or greater than 5 and less than or equal to 9, and wherein n is equal to or greater than m.

In a further embodiment, the poly/oligonucleotide of the invention is single-stranded and contains, preferably consists of, a 5' portion and a 3' portion, one of the portions further contains, preferably consists of, n G's, wherein the other portion contains, preferably consists of, p U's and q C's, wherein n, p and q are integers greater than zero, wherein p+q=m, wherein m is an integer up to 25, preferably equal to or greater than 5 and less than or equal to 9, and wherein n is equal to or greater than m.

In a further embodiment, the poly/oligonucleotide of the invention is fully or partially double-stranded, wherein one strand in the double-strand may further contain, preferably consist of, n U's, wherein the other strand in the double-strand contains, preferably consists of, p G's and q A's, wherein n, p and q are integers greater than zero, wherein p+q=m, wherein m is an integer up to 25, preferably equal to or greater than 11 and less than or equal to 21, and wherein n is equal to or greater than m.

In a further embodiment, the poly/oligonucleotide of the invention is single-stranded and may further contain, preferably consist of, a 5' portion and a 3' portion, wherein one of the portions contains, preferably consists of, n U's, and the other portion contains, preferably consists of, p G's and q A's. n, p and q are integers greater than zero, wherein p+q=m, wherein m is an integer up to 25, preferably equal to or greater than 11 and less than or equal to 21, and wherein n is equal to or greater than m.

In one embodiment of the invention the herein defined RNA poly/oligonucleotide, wherein one strand or a portion of a strand that makes up the at least one substantially, preferably fully double-stranded section contains n base pairs and preferably consists of p G:U and q G:C basepairs and r A:U basepairs, wherein p is an integer less than or equal to n, wherein q is an integer less than or equal to n−1, and r is an integer less or equal to n−1, and wherein p+q+r=n and n is an integer of at least 5, preferably 6-26.

In a further embodiment, the RNA poly/oligonucleotide of the invention is a single-stranded poly/oligonucleotide which has at least one stem-and-loop structure, and the at least one double-stranded section contained therein is the stem of the at least one single-stranded poly/oligonucleotide.

The invention further relates to the RNA poly/oligonucleotide as defined above, wherein n is greater than 100, preferably greater than 1000, more preferably greater than 2000, most preferably between 3000 and 5000.

In a preferred embodiment, the invention relates to RNA poly/oligonucleotide as defined above that show selective TLR7 and/or TLR8 activity. In a further embodiment the RNA poly/oligonucleotide prepared by the method defined herein or the RNA poly/oligonucleotide described herein does not contain AU base pairs and no unpaired U and shows selective TLR7 activity. In a more preferred embodiment of the invention the RNA poly/oligonucleotide as defined above that show selective TLR7 activity without the need of complexation to other reagents, especially an RNA poly/oligonucleotide as defined above, wherein the poly/oligonucleotide is substantially, preferably fully or partially double-stranded, wherein one strand in the double-strand contains, preferably consists of, n G's, wherein n is an integer between 20 and 100, and wherein the other strand in the double-strand contains, preferably consists of, p U's and q C's, wherein n, p and q are integers greater than zero, wherein p+q=m, wherein m is an integer up to 20, preferably equal to or greater than 5 and less than or equal to 9, and wherein n is equal to or greater than m.

In an alternative embodiment, the oligonucleotides show selective TLR7 activity without the need of complexation to an RNA poly/oligonucleotide as defined above, wherein n is greater than 100, preferably greater than 1000, more preferably greater than 2000, most preferably between 3000 and 5000.

In a preferred embodiment of the invention, the RNA poly/oligonucleotide as defined above, comprises one G:U base pair in each double-stranded section, and the G:U base pair is in the center of each double-stranded section.

In a further embodiment of the invention a RNA poly/oligonucleotide is provided showing selective TLR8 activity, wherein the G nucleoside in the G:U wobble base pair is adjacent on each side to C nucleosides.

In a further embodiment of the invention a RNA poly/oligonucleotide is provided comprising at least one U that is not involved in RNA base pairing, wherein the poly/oligonucleotide is capable of inducing an immune response, preferably a type I IFN response, wherein the immune response is enhanced by the addition of exogenous G nucleoside.

Moreover, the invention provides a pharmaceutical composition comprising at least one poly/oligonucleotide as defined above.

In one embodiment of the invention, the pharmaceutical composition further comprises at least one agent selected from an immunostimulatory agent, an anti-viral agent, an anti-bacterial agent, an anti-tumor agent, IFN-α, and IFN-β.

The invention further provides an in vitro method for inducing type I IFN production in a cell, comprising the steps of: contacting a cell with at least one poly/oligonucleotide as defined above, optionally mixed with a complexation agent, wherein the cell expresses TLR7 and is capable of producing an immune response, preferably an anti-viral response upon TLR7 activation.

DETAILED DESCRIPTION OF THE INVENTION

Figure 1:
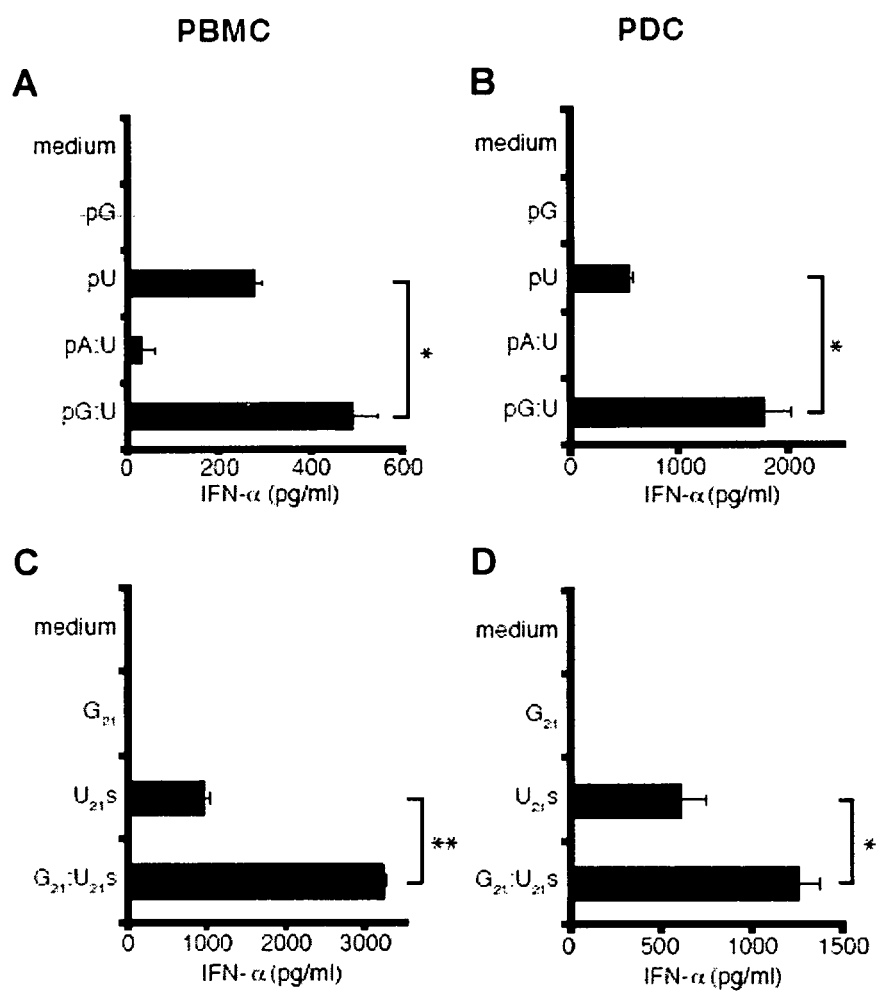
FIG. 1: Induction of IFN-α by polyU strands is enhanced by polyG counter-strands. Human PBMCs (A,C) or human PDCs (B,D) were stimulated with ssRNA or dsRNA complexed with Poly-L-Arginine. dsRNA was generated by hybridizing two required ssRNA oligonucleotides (pG, pU, pA, $G_{21}$ or $U_{21}$) in equal quantities (w/w). 20 h after stimulation, cell culture supernatants were assed for IFN-α by ELISA. Data shown are representative of 3 independent experiments presented as mean±standard error of mean (s.e.m.) (* P≤0.05, and ** P≤0.01: t-test).

Early studies showed that TLR7 was activated by genomic RNA from ssRNA viruses [4, 6, 17]. Further studies showed that short synthetic ssRNAs were able to stimulate TRL7 in a similar manner as single-stranded viral RNA [2, 6, 7, 21, 24].

Even though the stimulation of TLR7 by short ssRNAs has been described as being sequence-dependent (Hornung et al, 2004), a large number of ssRNAs with very different sequences have been reported to stimulate TLR7. Furthermore, even though uridine-rich sequences have been reported to be a molecular motif recognized by TLR7 (Diebold S S et al, 2006), it has also been reported that ORN lacking uridines were not immunostimulatory, and most ORN rich in guanosines and uridines were stimulatory for both, TLR7 and TLR8. While long RNA molecules activate both, TLR7 and TLR8, particular short oligoribonucleotide (ORN) that lack guanosines fail to activate TLR7. The structural basis for this distinction is unknown. Moreover, the biological impact of a differential recognition of RNA by TLR7 and TLR8 is unknown, and selective activation of human TLR7 by RNA has so far not been reported.

Surprisingly, the present inventors found that it was not the GU or U content of a RNA which determines its TLR7-activating and/or IFN-α-inducing activity, rather, it was the presence of a G:U wobble base pair, in particular, a G:U base pair in the context of a double-stranded structure. The inventors found that a single G·U wobble base pair within otherwise non-stimulatory RNA is sufficient to provide full TLR7 agonist activity. G·U base pairs form naturally in the secondary structure assumed by single-stranded RNA. Elimination of the G·U wobble base pair abolished TLR7 activity even when the overall base composition was maintained. The inventor showed that RNAs that form a G·U base pair are able to induce high levels of type I IFN secretion by plasmacytoid dendritic cells (PDC), but do not activate human monocytes. Moreover, phosphodiester ORN that form a G·U base pair when hybridized with poly guanosine (pG) show high and selective TLR7 activity without the need of complexation to other reagents. The identification of the minimal structural motif for TLR7 allows the design of RNA-based TLR7 selective agonists that act independently of additional components comparable to CpG oligonucleotides for TLR9. Furthermore, the present inventors found that an optimal IFN-α-inducing activity was observed when a G:U base pair was placed in the center of a double-stranded structure which has stability comparable to that of a double-stranded structure formed by 4-8 G:C base pairs or 10-20 A:U base pairs in addition to the G:U base pair. Furthermore, most of the ssRNAs disclosed in the prior art, which activated TLR7 also activated TLR8 (review Heil et al., 2004).

In summary, the present inventors found for the first time RNA poly- and oligonucleotides, which activated TLR7 specifically without activating TLR8. These TLR7-specific ligands are characterized by a G:U base pair in the center of a double-stranded structure which is formed by 4-8 G:C base pairs in addition to the G:U base pair. The present inventors found that short RNA stems were highly immunostimulatory, and selectively activated TLR7 when they contained at least one G·U wobble base pair. The G·U base pair therefore constitutes the so far unappreciated minimal structural motif sufficient to confer TLR7 agonist activity in single stranded RNA.

Moreover, because TLR7 is located in the endosomal compartments of certain immune cells, immunostimulatory RNAs have to be delivered to the endosomes for them to be able to stimulate TLR7. Complexation or transfection reagents, such as cationic polypeptides, are required for the cellular uptake and delivery of RNAs into the endosomes. Furthermore, since RNA with phosphodiester backbone is subject to hydrolysis as well as ribonuclease degradation, complexation or transfection agents are required for stabilizing RNA prior to its arrival in the target cell or subcellular compartment.

The present inventors found for the first time that certain TLR7-specific RNA ligands having phosphodiester backbone can be taken up by the cells, enter the endosomal compartments and activate TLR7 without being complexed with a complexation or transfection reagent. Some of these ligands are composed of a long poly-guanosine (polyG or pG) strand (3000-5000 nucleotides) and short ssRNA 6-8 nucleotides in length containing one U in the center of a stretch of 5-7 C's.

Thus, the inventors identified the first phosphodiester RNA ligand, which selectively stimulates TLR7 on its own, and therefore obviating the need for formulation with transfection reagents such as polycations.

The findings of the present inventors made it possible for the first time to develop TLR7-specific and highly active RNA agents which can be used for stimulating type I IFN production in vitro and in vivo and for treating or preventing diseases which can be treated or prevented by type I IFN, such as viral infections, immune disorders and cancer. Furthermore, the discovery of immunostimulatory RNAs, which do not require a complexation or transfection agent for delivery in vitro and in vivo offers great new research and clinical possibilities.

Definition

As used herein, "a" and "an" refer to not only a single individual, but also a group or species of entities unless otherwise noted.

All terms used herein bear the meanings that are established in the art unless otherwise noted. Techniques disclosed herein can be performed by a person skilled in the art following the present description and/or established protocols, such as those disclosed in *Molecular Cloning: A Laboratory Manual* (Sambrook et al., 1989, Cold Spring Harbour Laboratory, New York), *Current Protocols in Molecular Biology* (Ausubel et al., 2007, John Wiley & Sons, New York), and *Current Protocols in Immunology* (Coligan et al., 2007, John Wiley & Sons, New York).

As used herein, "oligonucleotide" refers to a nucleic acid molecule having 2-100 nucleotides and "polynucleotide" refers to a nucleic acid molecule having more than 100 nucleotides. All sequences are in the 5'->3' direction unless otherwise noted. n consecutive nucleotides X is written as Xn when n is an integer greater than zero. For example, XXXYXXXXXZXX is written as $X_3YX_5ZX_2$. When n is greater than 100, Xn can also be written as polyX or pX.

Method for Preparing a Polynucleotide or an Oligonucleotide

The present invention provides a method for preparing an RNA polynucleotide or oligonucleotide (hereinafter "poly/oligonucleotide") which is capable of inducing an immune response, preferably an anti-viral response, more preferably a type I IFN response, more specifically, an IFN-α response, comprising the steps of:

(a) identifying a nucleotide sequence which allows for the formation of at least one double-stranded section, wherein the at least one full double-stranded section comprises at least one G:U base pair, and wherein the at least one double-stranded section has a stability that is comparable to that of a double-stranded section composed of at least 4, preferably 4 to 8, G:C base pairs and at least one, preferably one G:U base pair or is comparable to a double-stranded section composed of at least 8, preferably 10 to 20, A:U base pairs and at least one, preferably one G:U, base pair;

(b) producing an RNA poly/oligonucleotide having the nucleotide sequence identified in (a); and (c) optionally testing the ability of the RNA produced in step (b) to induce a type I IFN response.

The poly/oligonucleotide may be produced by any suitable means known in the art, such as chemical synthesis and in vitro transcription. In the case of a double-stranded poly/oligonucleotide, the two strands may be produced by the same or different methods. The ability of a poly/oligonucleotide to induce a type I IFN response can be tested by any suitable methods known in the art, such as those disclosed in the Examples.

Polynucleotides and Oligonucleotides

The present invention provides an RNA poly/oligonucleotide, which is capable of inducing an immune response, preferably an antiviral response, more preferably a type I IFN response, most preferably an IFN-α response, obtained by the method described above. In particular, the present invention provides a poly/oligonucleotide which comprises at least one substantially, preferably fully double-stranded section, wherein the at least one double-stranded section comprises at least one G:U base pair, and wherein at least one double-stranded section has a stability that is comparable to that of a double-stranded section composed of at least 4, preferably 6 to 11, G:C base pairs and at least one, preferably one G:U, base pair or a double-stranded section composed of at least 10, preferably 10 to 21, A:U base pairs and at least one, preferably one G:U, base pair.

By "fully double-stranded", it is meant that the double-stranded section does not contain mismatches that compromise a minimal stability of the double-strand of said section. A section is fully double-stranded when the sequences of the two stretches of nucleic acid forming the section are 100% complementary to each other. Two nucleotides are said to be complementary to each other if they can form a base pair, either a Waston-Crick base pair (A-U, G-C) or a wobble base pair (U-G, U-A, I-A, I-U, I-C).

By "substantially fully double-stranded", it is meant that the double-stranded section as defined above may contain mismatches or single base insertions up to 10% of the total number of bases, provided the that the substantially fully double-stranded section maintains a minimal stability of the double-strand of said section.

The stability of a substantially, preferably fully double-stranded section can be determined by a skilled person using methods known in the art. In a preferred embodiment, the stability is determined by the software DNamelt (http://www.bioinfo.rpi.edu/applications/hybrid/) based on Markham N R & Zuker M (2005) and Markham N R & Zuker M (2008).

By "comparable" it is meant that the stability of a substantially, preferably fully double-stranded section is 75%-125%, preferably 80-120%, more preferably 90-110%, most preferably 95-105% of that of a double-stranded section composed of at least 4, preferably 6 to 11, G:C base pairs and at least one, preferably one G:U, base pair or a section composed of at least 8, preferably 10 to 21, A:U base pairs and at least one, preferably one G:U, base pair. Preferably, the stability of a substantially, preferably fully double-stranded section is within a range with the lower limit being 75%, preferably 80%, more preferably 90%, most preferably 95% of the stability of a double-stranded section composed of 4 G:C base pairs and one G:U base pair or a section composed of 10 A:U base pairs and one G:U base pair and the upper limit being 125%, preferably 120%, more preferably 110%, most preferably 105% of the stability of a double-stranded section composed of 8 G:C base pairs and one G:U base pair or a section composed of 20 A:U base pairs and one G:U base pair. In one embodiment, the one strand or a portion of a strand that forms the at least one fully double-stranded section contains, preferably consists of, n G's, and the other strand or a portion of a strand that forms the same at least one fully double-stranded section contains, preferably consists of, p U's and q C's, wherein n is an integer equal to or greater than 5 and less than or equal to 9, wherein p is an integer less than or equal to n, wherein q is an integer, and wherein p+q=n.

In one embodiment, the one strand or a portion of a strand that forms the at least one fully double-stranded section contains, preferably consists of, n U's, and the other strand or a portion of a strand that forms the same at least one fully double-stranded section contains, preferably consists of, p G's and q A's, wherein n is an integer equal to or greater than 11 and less than or equal to 21, wherein p is an integer less than or equal to n, wherein q is an integer, and wherein p+q=n.

In one embodiment, each fully double-stranded section comprises only one G:U base pair in the center of the fully double-stranded section. When the fully double-stranded section is composed of an odd number (2n+1) of base pairs, the center of the section is base pair number n+1. When the fully double-stranded section is composed of an even number, 2n, of base pairs, the center of the section can be either base pair number n or n+1.

In one embodiment, the poly/oligonucleotide is a double-stranded poly/oligonucleotide. In a preferred embodiment, the double-stranded poly/oligonucleotide is fully double-stranded. By "fully double-stranded" it is meant within the context of this preferred embodiment that the two strands forming the poly/oligonucleotide have the same length and have sequences which are 100% complementary to each other.

In one embodiment, one strand in the double strand contains, preferably consists of, n G's, and the other strand in the double strand contains, preferably consists of, p U's and q C's, wherein n is an integer equal to or greater than 5 and less than or equal to 9, wherein p is an integer less than or equal to n, wherein q is an integer, and wherein p+q=n. In a preferred embodiment, p equals 1 and U is in the center of the strand containing or consisting of U and C's.

In a preferred embodiment, one strand in the double strand contains, preferably consists of, n U's, and the other strand in the double strand contains, preferably consists of, p G's and q A's, wherein n is an integer equal to or greater than 11 and less than or equal to 21, wherein p is an integer less than or equal to n, wherein q is an integer, and wherein p+q=n. In a preferred embodiment, p equals 1 and G is in the center of the strand containing or consisting of G and A's.

In one embodiment of the invention the herein defined RNA poly/oligonucleotide, wherein one strand or a portion of a strand that makes up the at least one substantially, preferably fully double-stranded section contains n base pairs and preferably consists of p G:U and q G:C basepairs and r A:U basepairs, wherein p is an integer less than or equal to n, wherein q is an integer less than or equal to n−1, and r is an integer less or equal to n−1, and wherein p+q+r=n and n is an integer of at least 5, preferably 6-26.

The position of the G-U base pairs in the double stranded poly/oligonucleotides as defined herein is not limited and may be at any position well-off the center in the double stranded section, preferably the G-U base pairs are located in the center in the double stranded section.

The double-stranded section preferably contains uridines (one or multiple) exclusively in the form of G·U base pairs.

Specific Examples of a fully double-stranded poly/oligonucleotide include:

$G_5+C_2UC_2$ (CCUCC),
$G_6+C_3UC_2$ (CCCUCC),
$G_6+C_2UC_3$ (CCUCCC),
$G_7+C_3UC_3$ (CCCUCCC),
$G_8+C_4UC_3$ (CCCCUCCC),
$G_8+C_3UC_4$ (CCCCUCCC),
$G_9+C_4UC_4$ (CCCCUCCCC),
$U_{11}+A_5GA_5$,
$U_{12}+A_6GA_5$,
$U_{12}+A_5GA_6$,
$U_{13}+A_6GA_6$,
$U_{14}+A_7GA_6$,
$U_{14}+A_6GA_7$,
$U_{15}+A_7GA_7$, $U_{16}+A_8GA_7$,
$U_{16}+A_7GA_8$,
$U_{17}+A_8GA_8$,
$U_{18}+A_9GA_8$,
$U_{18}+A_8GA_9$,
$U_{19}+A_9GA_9$,
$U_{20}+A_{10}GA_9$,
$U_{20}+A_9GA_{10}$,
$U_{21}+A_{10}GA_{10}$,
$U_{21}+A_5GA_{10}GA_4$.

In another preferred embodiment, the double-stranded poly/oligonucleotide is partially double-stranded. By "partially double-stranded" it is meant that the two strands forming the poly/oligonucleotide have different lengths, sequences which are not 100% complementary to each other, or both. In other words, the fully double-stranded section is connected with a single-stranded structure at one or both ends.

In one embodiment, one strand in the double strand contains, preferably consists of, n G's, and the other strand in the double strand contains, preferably consists of, p U's and q C's, wherein n, p and q are integers greater than zero, wherein p+q=m, wherein m is an integer up to 25, preferably equal to or greater than 5 and less than or equal to 9, and wherein n is greater than m.

In one embodiment, n is less than or equal to 100. In another embodiment, n is greater than 100, preferably greater than 1000. In a poly/oligonucleotide preparation containing more than one poly/oligonucleotide molecule, n may be different in different poly/oligonucleotide molecules. In other words, a poly/oligonucleotide preparation of the present invention may contain a mixture of molecules, which have different length in the one strand which contains or consists of n G's. In a preferred embodiment, the G-containing strand is a poly-guanosine (polyG or pG) containing about 3000-5000 G's obtained by conventional enzymatic processes, such as polynucleotide phosphorylase (PNPase) enzymatic reaction. In a preferred embodiment, p equals 1 and U is in the center of the strand containing or consisting of U's and C's.

In one embodiment, one strand in the double strand contains, preferably consists of, n U's, and the other strand in the double strand contains, preferably consists of, p G's and q A's, wherein n, p and q are integers greater than zero, wherein p+q=m, wherein m is an integer up to 25, preferably equal to or greater than 11 and less than or equal to 21, and wherein n is greater than m.

In one embodiment, n is less than or equal to 100. In another embodiment, n is greater than 100, preferably greater than 1000. In a poly/oligonucleotide preparation containing more than one poly/oligonucleotide, n may be different in different poly/oligonucleotide molecules. In other words, a poly/oligonucleotide preparation of the present invention may contain a mixture of molecules, which have different length in the one strand which contains or consists of n U's. In a preferred embodiment, the U-containing strand is a poly-uridine (polyU or pU) comprising about 3000-5000 U's obtained by conventional enzymatic processes, such as polynucleotide phosphorylase (PNPase). In a preferred embodiment, p equals 1 and G is in the center of the strand containing or consisting of G and A's.

Examples of a partially double-stranded poly/oligonucleotide include:

$Gn+C_2UC_2$ (CCUCC), wherein n is an integer greater than 5;
$Gn+C_3UC_2$ (CCCUCC), wherein n is an integer greater than 6;
$Gn+C_2UC_3$ (CCUCCC), wherein n is an integer greater than 6;
$Gn+C_3UC_3$ (CCCUCCC), wherein n is an integer greater than 7;
$Gn+C_4UC_3$ (CCCCUCCC), wherein n is an integer greater than 8;
$Gn+C_3UC_4$ (CCCUCCCC), wherein n is an integer greater than 8;
$Gn+C_4UC_4$ (CCCCUCCCC), wherein n is an integer greater than 9;
$Gn+C_2UC_3UC_2$ (CCUCCCUCC), wherein n is an integer greater than 9
$Un+A4G4$, wherein n is an integer greater than 9;
$Un+A4G5$, wherein n is an integer greater than 10;
$Un+A5GA4$, wherein n is an integer greater than 10;
$Un+A_5GA_5$, wherein n is an integer greater than 11;
$Un+A_6GA_5$, wherein n is an integer greater than 12;
$Un+A_5GA_6$, wherein n is an integer greater than 12;
$Un+A_6GA_6$, wherein n is an integer greater than 13;
$Un+A_7GA_6$, wherein n is an integer greater than 14;
$Un+A_6GA_7$, wherein n is an integer greater than 14;
$Un+A_7GA_7$, wherein n is an integer greater than 15;
$Un+A_8GA_7$, wherein n is an integer greater than 16;
$Un+A_7GA_8$, wherein n is an integer greater than 16;
$Un+A_8GA_8$, wherein n is an integer greater than 17;
$Un+A_9GA_8$, wherein n is an integer greater than 18;
$Un+A_8GA_9$, wherein n is an integer greater than 18;
$Un+A_9GA_9$, wherein n is an integer greater than 19;
$Un+A_{10}GA_9$, wherein n is an integer greater than 20;
$Un+A_9GA_{10}$, wherein n is an integer greater than 20;
$Un+A_{10}GA_{10}$, wherein n is an integer greater than 21;
$Un+A_5GA_{10}GA_4$, wherein n is an integer greater than 21;

Preferably, n is greater than 1000, more preferably greater than 3000, most preferably about 3000-5000 in the examples above. Most preferably, Gn is polyG containing about 3000-5000 G's and obtained from conventional enzymatic processes, such as polynucleotide phosphorylase (PNPase) enzymatic reaction.

In one embodiment, the poly/oligonucleotide is a single-stranded poly/oligonucleotide. In a preferred embodiment, the single-stranded poly/oligonucleotide is completely self-complementary. By "completely self-complementary" it is meant that the 5' half of the molecule is 100% complementary to the 3' half of the molecule. As a result, the molecule forms a single fully double-stranded section.

In one embodiment, one of the 5' and 3' halves contains, preferably consists of, n G's, and the other half contains, preferably consists of, p U's and q C's, wherein n is an integer equal to or greater than 5 and less than or equal to 9, wherein p is an integer less than or equal to n, wherein q is an integer, and wherein p+q=n. In a preferred embodiment, p equals 1 and U is in the center of the half containing or consisting of U and C's.

In one embodiment, one of the 5' and 3' halves contains, preferably consists of, n U's, and the other half contains, preferably consists of, p G's and q A's, wherein n is an integer equal to or greater than 11 and less than or equal to 21, wherein p is an integer less than or equal to n, wherein q is an integer, and wherein p+q=n. In a preferred embodiment, p equals 1 and G is in the center of the half containing or consisting of G and A's.

Examples of a completely self-complementary single-stranded poly/oligonucleotide include:

$C_2UC_2G_5$
$C_3UC_2G_6$,
$C_2UC_3G_6$,
$C_3UC_3G_7$, $C_4UC_3G_8$,
$C_3UC_4G_8$,
$C_4UC_4G_9$,
$G_5C_2UC_2$,
$G_6C_3UC_2$,
$G_6C_2UC_3$,
$G_7C_3UC_3$,
$G_8C_4UC_3$,
$G_8C_3UC_4$,
$G_9C_4UC_4$,
$A_5GA_5U_{11}$,
$A_6GA_5U_{12}$,
$A_5GA_6U_{12}$,
$A_6GA_6U_{13}$,
$A_7GA_6U_{14}$,
$A_6GA_7U_{14}$,
$A_7GA_7U_{15}$,
$A_8GA_7U_{16}$,
$A_7GA_8U_{16}$,
$A_8GA_8U_{17}$,
$A_9GA_8U_{18}$,
$A_8GA_9U_{18}$,
$A_9GA_9U_{19}$,
$A_{10}GA_9U_{20}$,
$A_9GA_{10}U_{20}$,
$A_{10}GA_{10}U_{21}$,
$A_5GA_{10}GA_4U_{21}$,
$U_{11}A_5GA_5$,
$U_{12}A_6GA_5$,
$U_{12}A_5GA_6$,
$U_{13}A_6GA_6$,
$U_{14}A_7GA_6$,
$U_{14}A_6GA_7$,
$U_{15}A_7GA_7$,
$U_{16}A_8GA_7$,
$U_{16}A_7GA_8$,
$U_{17}A_8GA_8$,
$U_{18}A_9GA_8$,
$U_{18}A_8GA_9$,
$U_{19}A_9GA_9$,
$U_{20}A_{10}GA_9$,
$U_{20}A_9GA_{10}$,
$U_{21}A_{10}GA_{10}$,
$U_{21}A_5GA_{10}GA_4$.

In another preferred embodiment, the single-stranded poly/oligonucleotide has at least one stem-and-loop structure, and the at least one fully double-stranded section is the stem of the at least one single-stranded poly/oligonucleotide.

The formation of a stem-and-loop structure can be readily predicted by a person skilled in the art on the basis of the nucleotide sequence of the poly/oligonucleotide and experimentally verified by methods known in the art. For example, a ssRNA oligonucleotide can be digested with a single-strand-specific RNase and analysed on a denaturing gel.

The exact size and the sequence of the loop are not critical; it is only critical that the loop does not adversely affect the formation and the stability of the stem.

The present invention relates to poly/oligonucleotides having a structure defined by the following general formula I:

$$X_nG/UV_mN_oW_mU/GY_n \quad \text{(Formula I)},$$

wherein if $X_n$ is followed by G then $W_m$ is followed U, or if $X_n$ is followed by U then $W_m$ is followed by G (in order to form a wobble base pair), wherein
$2 \leq n \leq 12$, $2 \leq m \leq 12$ and $2 \leq o \leq 12$;
X defines any base that forms a Watson-Crick base pair with corresponding bases in Y;
V defines any base that forms a Watson-Crick base pair with corresponding bases in W in an RNA stem structure, and
N is any base in a loop.

Also encompassed are repeats of the base paired cassettes. The total length of the RNA containing the pattern of Formula I is preferably 15 to 45 bases.

Preferred poly/oligonucleotides of the invention have a structure defined by the following general formula II and III, defining two separate RNA strands containing the cassettes:

$$5'X_nG/UV_m3' \quad \text{(Formula II)}$$

$$5'_oW_mU/GY_n3' \quad \text{(Formula III)},$$

wherein G/U and U/G are selected that a wobble base pair forms,
with $2 \leq n \leq 12$, $2 \leq m \leq 12$ and $2 \leq o \leq 12$;
X defines any base that forms a Watson-Crick base pair with corresponding bases in Y;
V defines any base that forms a Watson-Crick base pair with corresponding bases in W in an RNA stem structure, and
N is any base in a loop,
The total length of these separate RNA strands of Formula II and III is preferably 5 bases to 45 bases.

Most preferred poly/oligonucleotides of the invention having at least one stem-and-loop structure have a structure defined by the following general formula II and III, defining two separate RNA strands containing the cassettes:

$$5'X_nG/UV_m3' \quad \text{(Formula II)}$$

$$5'_oW_mU/GY_n3' \quad \text{(Formula III)},$$

wherein G/U and U/G are selected that a wobble base pair forms,
with $2 \leq n \leq 12$, $2 \leq m \leq 12$ and $2 \leq o \leq 12$;
with X denoting Gs or Cs that form Watson-Crick bases pairs with corresponding G and C bases in Y, and V represents Gs or Cs that form Watson-Crick base pairs with corresponding bases in W.

Repeats of the base paired cassettes (i.e. multiple G·U base pairs in double stranded structures) will have activity.

A preferred total length of these separate RNA strands is 5 bases to 45 bases.

In one embodiment of the RNA poly/oligonucleotide of the invention, the one strand or a portion of a strand that forms the at least one substantially, preferably fully double-stranded section contains n base pairs and preferably consists of p G:U and q G:C basepairs, wherein p is an integer less than or equal to n, wherein q is an integer less than or equal to n−1, and wherein p+q=n and n is an integer of at least 5, preferably 6-15.

In a further embodiment, RNA poly/oligonucleotide of the invention, the one strand or a portion of a strand that forms the at least one substantially, preferably fully double-stranded section contains n base pairs and preferably consists of p G:U and q A:U, wherein p is an integer less than or equal to n, wherein q is an integer less than or equal to n−1, and wherein p+q=n and n is an integer of at least 9, preferably 12-26.

The design of such RNA poly/oligonucleotide as defined above allows the generation of RNAs having TLR7 and TLR8 activity.

In one embodiment, one of the two portions of the single-stranded poly/oligonucleotide which make up the at least one fully double-stranded stem structure contains, preferably consists of, n G's, and the other portion which forms the same at least one double-stranded stem structure contains, preferably consists of, p U's and q C's, wherein n is an integer equal to or greater than 5 and less than or equal to 9, wherein p is an integer less than or equal to n, wherein q is an integer, and wherein p+q=n. In a preferred embodiment, p equals 1 and U is in the center of the portion containing or consisting of U and C's.

In a specific embodiment, the single-stranded poly/oligonucleotide contains, preferably consists of, two portions, a 5' portion and a 3' portion, wherein one of the two portions contains, preferably consists of, n G's, wherein the other portion contains, preferably consists of, p U's and q C's, wherein n, p and q are integers greater than zero, wherein p+q=m, wherein m is an integer up to 25, preferably equal to or greater than 5 and less than or equal to 9, and wherein n is greater than m. In one embodiment, n is less than or equal to 100. In another embodiment, n is greater than 100, preferably greater than 1000, more preferably greater than 3000, most preferably on the order of 3000-5000. In certain embodiments, n may be different in different molecules in a poly/oligonucleotide preparation of the present invention. In a preferred embodiment, p equals 1 and U is in the center of the portion containing or consisting of U and C's.

In one embodiment, one of the two portions of the single-stranded poly/oligonucleotide which make up the at least one fully double-stranded stem structure contains, preferably consists of, n U's, and the other portion which forms the same at least one fully double-stranded stem structure contains, preferably consists of, p G's and q A's, wherein n is an integer equal to or greater than 11 and less than or equal to 21, wherein p is an integer less than or equal to n, wherein q is an integer, and wherein p+q=n. In a preferred embodiment, p equals 1 and G is in the center of the portion containing or consisting of G and A's.

In a specific embodiment, the single-stranded poly/oligonucleotide contains, preferably consists of, two portions, a 5' portion and a 3' portion, wherein one of the two portions contains, preferably consists of, n U's, and the other portion contains, preferably consists of, p G's and q A's, wherein n, p and q are integers greater than zero, wherein p+q=m, wherein m is an integer up to 25, preferably equal to or greater than 11 and less than or equal to 21, and wherein n is greater than m. In one embodiment, n is less than or equal to 100. In another embodiment, n is greater than 100, preferably greater than 1000, more preferably greater than 3000, most preferably on the order of 3000-5000. In certain embodiments, n may be different in different molecules in a poly/oligonucleotide preparation of the present invention. In a preferred embodiment, p equals 1 and G is in the center of the portion containing or consisting of G and A's.

Examples of a single-stranded poly/oligonucleotide having at least one stem-and-loop structure include:

$C_2UC_2Gn$, wherein n is an integer equal to or greater than 4; preferably greater than 8 to 9.
$C_3UC_2Gn$, wherein n is an integer greater than 6;
$C_2UC_3Gn$, wherein n is an integer greater than 6;
$C_3UC_3Gn$, wherein n is an integer greater than 7;
$C_4UC_3Gn$, wherein n is an integer greater than 8;
$C_3UC_4Gn$, wherein n is an integer greater than 8;
$C_4UC_4Gn$, wherein n is an integer greater than 9;
$GnC_2UC_2$, wherein n is an integer greater than 5;
$GnC_3UC_2$, wherein n is an integer greater than 6;
$GnC_2UC_3$, wherein n is an integer greater than 6;
$GnC_3UC_3$, wherein n is an integer greater than 7;
$GnC_4UC_3$, wherein n is an integer greater than 8;
$GnC_3UC_4$, wherein n is an integer greater than 8;
$GnC_4UC_4$, wherein n is an integer greater than 9;
$A_5GA_5Un$, wherein n is an integer greater than 11;
$A_6GA_5Un$, wherein n is an integer greater than 12;
$A_5GA_6Un$, wherein n is an integer greater than 12;
$A_6GA_6Un$, wherein n is an integer greater than 13;
$A_7GA_6Un$, wherein n is an integer greater than 14;
$A_6GA_7Un$, wherein n is an integer greater than 14;
$A_7GA_7Un$, wherein n is an integer greater than 15;
$A_8GA_7Un$, wherein n is an integer greater than 16;
$A_7GA_8Un$, wherein n is an integer greater than 16;
$A_8GA_8Un$, wherein n is an integer greater than 17;
$A_9GA_8Un$, wherein n is an integer greater than 18;
$A_8GA_9Un$, wherein n is an integer greater than 18;
$A_9GA_9Un$, wherein n is an integer greater than 19;
$A_{10}GA_9Un$, wherein n is an integer greater than 20;
$A_9GA_{10}Un$, wherein n is an integer greater than 20;
$A_{10}GA_{10}Un$, wherein n is an integer greater than 21;
$A_5GA_{10}GA_4Un$, wherein n is an integer greater than 21;
$UnA_5GA_5$, wherein n is an integer greater than 11;
$UnA_6GA_5$, wherein n is an integer greater than 12;
$UnA_5GA_6$, wherein n is an integer greater than 12;
$UnA_6GA_6$, wherein n is an integer greater than 13;
$UnA_7GA_6$, wherein n is an integer greater than 14;
$UnA_6GA_7$, wherein n is an integer greater than 14;
$UnA_7GA_7$, wherein n is an integer greater than 15;
$UnA_8GA_7$, wherein n is an integer greater than 16;
$UnA_7GA_5$, wherein n is an integer greater than 16;
$UnA_8GA_8$, wherein n is an integer greater than 17;
$UnA_9GA_8$, wherein n is an integer greater than 18;
$UnA_8GA_9$, wherein n is an integer greater than 18;
$UnA_9GA_9$, wherein n is an integer greater than 19;
$UnA_{10}GA_9$, wherein n is an integer greater than 20;
$UnA_9GA_{10}$, wherein n is an integer greater than 20;
$UnA_{10}GA_{10}$, wherein n is an integer greater than 21;
$UnA_5GA_{10}GA_4$, wherein n is an integer greater than 21.

Preferably, n is greater than 1000, more preferably 3000, even more preferably on the order of 3000-5000 in the examples above.

The present invention also provides RNA poly/oligonucleotides that have the properties of activating TLR7 via the herein described G·U containing cassettes, but do not require additional facilitators of cellular uptake (e.g. lipids, poly cations, transfection reagents). These RNA poly/oligonucleotides form at least one G·U cassette when hybridized or connected via a loop to a highly G rich strand. G rich strands are either obtained by standard synthesis (preferred length 20-100 bp), or by enzymatic synthesis with an optimal length between 1000 and 5000 bases. Such strands of due to the enzymatic process poorly defined length are commonly synthesized by polynucleotide phosphorylase (PNPase). It is likely that the presence of few non-G bases (e.g. ≥⅙ of the bases could be I, A, U, C) will not interfere with the properties of the G rich strand. It is also expected that modifications known to stabilize RNA (e.g. desoxinucleotides, phosphothioates, etc.) will not restrict activity, and may thus be desirable.

The present invention also provides Um+Gn which is capable of inducing an immune response, in particular anti-viral response, more particular a type I IFN response, more specifically, an IFN-α response, wherein both, m and n, are integers between 1000-5000, and wherein m is greater than or equal to n. These nucleic acids are generated enzymatically by Polynucleotide Phosphorylase (PNPase).

In preferred embodiments, the poly/oligonucleotide of the invention is specifically recognized by and/or specifically activates TLR7 without being recognized by or activating TLR8.

Activity conferred by the G:U base pair can be readily determined by testing the RNA poly/oligonucleotide of the invention (such as those consisting exclusively of G·U and G:C base pairs), whether the immune stimulatory activity is lost when either one of the following mutations is applied:
a) The U of all G·U base pairs and the G of flanking G:C base pairs swap positions (in this test the overall base composition is maintained) or b) The G of all G·U base pairs is mutated to A.

Binding of a poly/oligonucleotide to TLR7 and/or TLR8 can be readily determined by methods known in the art. For example, a poly/oligonucleotide conjugated to a label (e.g., a radioactive molecule, a fluorescent molecule, an enzyme) can be delivered to cells expressing TLR7 and/or TLR8, and the binding of the labelled poly/oligonucleotide to TLR7 and/or TLR8 may be determined using techniques such as gel electrophoresis, microscopy, X-ray crystallography. Activation of TLR7 and/or TLR8 by a poly/oligonucleotide can also be readily determined by methods known in the art. For example, cells expressing TLR7 and/or TLR8 can be stimulated with a poly/oligonucleotide, and the production of type I IFN (in particular, IFN-α) and IL-12 can be used as readouts for the activation of TLR7 and TLR8, respectively. PDCs obtained from wild-type, TLR7$^{-/-}$ and TLR8$^{-/-}$ mice are ideal for such tests. Activation of TLR7 and/or TLR8 upon stimulation by a poly/oligonucleotide can also readily determined by detecting Overexpression of human and/or mouse TLR7 or TLR8 in non-immune reporter cells (e.g. HEK293T cells). Gene silencing may be used to reduce TLR7/8 expression. Gene silencing activity may be combined with the present structural requirements. Within the 16-21 bp siRNA duplex that usually consists exclusively of Watson-Crick base pairs G:U base pairs can be introduced without an expected penalty to the silencing activity, as long as the alterations to introduce G·U base pairs are limited to the sense strand.

The G·U base pair containing cassettes as defined herein may also be inserted into RNAs that exert an additional function, for example siRNA, ribozymes, aptamers.

TLR7-specific ligands include poly/oligonucleotides in which one strand or a portion of a strand that forms the at least one fully double-stranded section contains, preferably consists of, n G's, and the other strand or a portion of a strand that forms the same at least one fully double-stranded section contains, preferably consists of, p U's and q C's, wherein n is an integer equal to or greater than 5 and less than or equal to 9, wherein p is an integer less than or equal to n, wherein q is an integer, and wherein p+q=n.

The poly/oligonucleotide may contain any naturally-occurring, synthetic, modified nucleotides, or a mixture thereof, as long as the synthetic and/or modified nucleotides do not compromise (i.e., reduce) the type I IFN-inducing activity of the poly/oligonucleotide. The poly/oligonucleotide may contain any naturally-occurring, synthetic, modified internucleoside linkages, or a mixture thereof, as long as the linkages do not compromise the type I IFN-inducing activity of the poly/oligonucleotide.

In a further embodiment of the invention a RNA poly/oligonucleotide is provided showing selective TLR8 activity, wherein the U nucleoside in the G:U wobble base pair is adjacent on each side to G bases. The RNA poly/oligonucleotide showing selective TLR8 activity may be single stranded or partially double stranded. Preferably the RNA poly/oligonucleotide having G nucleoside in the G-U wobble base pair adjacent to C nucleoside at each side of the G:U wobble base pair, forms a hairpin structure as defined herein, wherein n is between 5 and 100, preferably 20 and 100, and. Said RNA poly/oligonucleotide shows highly selective TLR8 activity. Said RNA poly/oligonucleotide showing selective TLR8 activity, preferably has at least 2 adjacent base pairs on each side of the G:U wobble base pair. The term "selective TLR8 activity" as used herein means the RNA poly/oligonucleotide as defined above shows TLR8 activity but no TLR7 activity.

TLR7-specific ligands also include poly/oligonucleotides capable of inducing an immune response that comprise at least one uridine, preferably polyuridine, that is/are not involved in RNA base pairing, wherein the immune response, preferably a type I IFN response, is enhanced by the addition of exogenous G nucleoside, whereby base pairing with guanosine nucleoside enhances the activity of uridine to activate.

Various methods for producing poly/oligonucleotides are known in the art, including, but are not limited to, chemical synthesis and in vitro transcription.

The poly/oligonucleotide may be modified covalently or non-covalently to improve its chemical stability, resistance to nuclease degradation, ability to across cellular and/or subcellular membranes, target (organ, tissue, cell type, subcellular compartment)-specificity, pharmacokinetic properties, biodistribution, or any combinations thereof. For example, phosphorothioate linkage(s) and/or pyrophosphate linkage(s) may be introduced to enhance the chemical stability and/or the nuclease resistance of an RNA poly/oligonucleotide. In another example, the poly/oligonucleotide may be covalently linked to one or more lipophilic group(s) or molecule(s), such as a lipid or a lipid-based molecule, preferably cholesterol or a derivative thereof. Preferably, the modification does not comprise the type I IFN-inducing activity of the poly/oligonucleotide. Alternatively, a reduction in the type I IFN-inducing activity of the poly/oligonucleotide caused by the modification is off-set by an increase in the stability and/or delivery and/or other properties as described above.

The poly/oligonucleotide of the present invention may have one or more of the features described above in any combinations.

The present invention also provides a poly/oligonucleotide preparation comprising at least one poly/oligonucleotide of the present invention. The poly/oligonucleotide preparation of the present invention may comprise two or more different poly/oligonucleotides. Preferably, the two or more different poly/oligonucleotides comprised in the same preparation share the same fully double-stranded section and have similar structure. The variations in the chemical compositions of the poly/oligonucleotides in a preparation may result from the method of preparation.

Pharmaceutical Composition

The present invention provides a pharmaceutical composition comprising at least one of the RNA polynucleotide or oligonucleotide (poly/oligonucleotide) of the invention described above and a pharmaceutically acceptable carrier.

By "at least one" it is meant that one or more poly/oligonucleotide preparation(s) of the same or different poly/oligonucleotide(s) can be used together.

In one embodiment, the pharmaceutical composition further comprises an agent, which facilitates the delivery of the poly/oligonucleotide into a cell, in particular, into the endosomal compartments of the cell.

In one embodiment, the delivery agent is a complexation agent, which forms a complex with the poly/oligonucleotide and facilitates the delivery of the poly/oligonucleotide into cells. Complexation agents are also referred to as "transfection agents" in the art. Any complexation agent, which is compatible with the intended use of the pharmaceutical composition can be employed. Examples for transfection agents are Protamine(s). Examples of complexation agents include polymers and biodegradable microspheres. The polymer is preferably a cationic polymer, more preferably a cationic lipid. Examples of a polymer include polyethylenimine (PEI) such as in vivo-jetPEI™ (PolyPlus) and collagen derivatives. Examples of biodegradable microspheres include liposomes, virosomes, stable-nucleic-acid-lipid particles (SNALPs), ISCOMATRIX® (CSL Limited), and poly (D,L-lactide-co-glycolide) copolymer (PLGA) microspheres.

In another embodiment, the delivery agent is a virus, preferably a replication-deficient virus. The poly/oligonucleotide to be delivered is contained in the viral capsule and the virus may be selected based on its target specificity. Examples of useful viruses include polymyxoviruses which target upper respiratory tract epithelia and other cells, hepatitis B virus which targets liver cells, influenza virus which targets epithelial cells and other cells, adenoviruses which targets a number of different cell types, papilloma viruses which targets epithelial and squamous cells, herpes virus which targets neurons, retroviruses such as HIV which targets CD4$^+$ T cells, dendritic cells and other cells, modified Vaccinia Ankara which targets a variety of cells, and oncolytic viruses which target tumor cells. Examples of oncolytic viruses include naturally occurring wild-type Newcastle disease virus, attenuated strains of reovirus, vesicular stomatitis virus (VSV), and genetically engineered mutants of herpes simplex virus type 1 (HSV-1), adenovirus, poxvirus and measles virus.

In addition to being delivered by a delivery agent, the poly/oligonucleotide and/or the pharmaceutical composition can be delivered into cells via physical means such as electroporation, shock wave administration, ultrasound triggered transfection, and gene gun delivery with gold particles.

The pharmaceutical composition may further comprise another agent such as an agent that stabilizes the oligonucleotide. Examples of a stabilizing agent include a protein that complexes with the oligonucleotide to form an iRNP, chelators such as EDTA, salts, and RNase inhibitors.

In certain embodiments, the pharmaceutical composition further comprises one or more pharmaceutically active therapeutic agent(s). Examples of a pharmaceutically active agent include immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. Preferably, the pharmaceutically active agent is selected from the group consisting of an immunostimulatory agent, an anti-viral agent and an anti-tumor agent. The more than one pharmaceutically active agents may be of the same or different category.

The pharmaceutical composition may be formulated in any way that is compatible with its therapeutic application, including intended route of administration, delivery format and desired dosage. Optimal pharmaceutical compositions may be formulated by a skilled person according to common general knowledge in the art, such as that described in Remington's Pharmaceutical Sciences (18th Ed., Gennaro A R ed., Mack Publishing Company, 1990).

The pharmaceutical composition may be formulated for instant release, controlled release, timed-release, sustained release, extended release, or continuous release.

The pharmaceutical composition may be administered by any route known in the art, including, but not limited to, topical, enteral and parenteral routes, provided that it is compatible with the intended application. Topic administration includes, but is not limited to, epicutaneous, inhalational, intranasal, vaginal administration, enema, eye drops, and ear drops. Enteral administration includes, but is not limited to, oral, rectal administration and administration through feeding tubes. Parenteral administration includes, but is not limited to, intravenous, intraarterial, intramuscular, intracardiac, subcutaneous, intraosseous, intradermal, intrathecal, intraperitoneal, transdermal, transmucosal, and inhalational administration. In case of tumours or cancer, a preferred route of administration is an intra or peritumoral injection.

In a preferred embodiment, the pharmaceutical composition is for local (e.g., mucosa, skin) applications, such as in the form of a spray (i.e., aerosol) preparation.

The pharmaceutical composition may be used for prophylactic and/or therapeutic purposes. For example, a spray (i.e., aerosol) preparation may be used to strengthen the anti-viral capability of the nasal and the pulmonary mucosa.

The present invention also relates to prodrugs of the herein defined RNA poly/oligonucleotides having immune-stimulatory activity. An Example for a suitable prodrug is a linear RNA which is designed to form dsRNA sections containing G·U as a central secondary structure. Further prodrugs of the RNA poly/oligonucleotide as defined herein, include RNA poly/oligonucleotides which are chemically modified in either the G or the U in a fashion that in an organism the RNA poly/oligonucleotide is reverted to the active G and/or U, for example derivates of G and/or U that form an G·U equivalent.

The optimal dosage, frequency, timing and route of administration can be readily determined by a person skilled in the art on the basis of factors such as the disease or condition to be treated, the severity of the disease or condition, the age, gender and physical status of the patient, and the presence or absence of previous treatment.

In Vitro Applications

The present application provides the in vitro use of the RNA poly/oligonucleotide of the invention described above. In particular, the present application provides the use of at least one poly/oligonucleotide for inducing an anti-viral response, in particular, a type I IFN response, more specifically, an IFN-α response, in vitro.

The present invention provides an in vitro method for stimulating an anti-viral response, in particular, a type I IFN response, more specifically, an IFN-α response in a cell, comprising the steps of:
  (a) mixing at least one poly/oligonucleotide of the invention described above with a complexation agent; and
  (b) contacting a cell with the mixture of (a), wherein the cell expresses TLR7 and is capable of producing an anti-viral response upon TLR7 activation.

The present invention provides an alternative in vitro method for stimulating an anti-viral response, in particular, a type I IFN response, more specifically, an IFN-α response in a cell, comprising the steps of: contacting a cell with at least one poly/oligonucleotide of the invention described above, which is optionally mixed with a complexation agent, wherein the cell expresses TLR7 and is capable of producing an anti-viral response upon TLR7 activation.

The cells may express TLR7 endogenously and/or exogenously from an exogenous nucleic acid (RNA or DNA). The exogenous DNA may be a plasmid DNA, a viral vector, or a portion thereof. The exogenous DNA may be integrated into the genome of the cell or may exist extra-chromosomally. The cells include, but are not limited to, primary immune cells, primary non-immune cells, and cell lines. Immune cells include, but are not limited to, peripheral blood mononuclear cells (PBMC), plasmacytoid dendritic cells (PDC), myeloid dendritic cells (MDC), macrophages, monocytes, B cells, natural killer cells, granulocytes, CD4+

T cells, CD8+ T cells, and NKT cells. Among these cells, plasmacytoid dendritic cells (PDC), which are a subpopulation of peripheral blood mononuclear cells (PBMC), express TLR7 endogenously. Non-immune cells include, but are not limited to, fibroblasts, endothelial cells, epithelial cells, and tumor cells. Cell lines may be derived from immune cells or non-immune cells, which do or do not express TLR7 endogenously.

Whether a cell expresses TLR7 can be readily determined by a skilled person using standard techniques such as western blotting, RT-PCR, and northern blotting.

Whether a cell is capable of producing an anti-viral response upon TLR7 activation can be readily determined by a skilled person using a known TLR7 ligand and standard assays for cytokine detection such as ELISA, quantitative or semi-quantitative RT-PCR.

In Vivo Applications

The present application provides the in vivo use of the RNA poly/oligonucleotide of the invention described above.

In particular, the present application provides at least one RNA poly/oligonucleotide for inducing an anti-viral response, in particular, a type I IFN response, more specifically, an IFN-α response, in a vertebrate animal, in particular, a mammal. The present application further provides at least one RNA poly/oligonucleotide for preventing and/or treating a disease and/or disorder in a vertebrate animal, in particular, a mammal, in medical and/or veterinary practice. The present application further provides RNA poly/oligonucleotides for enhancing humoral immunity. The invention also provides RNA poly/oligonucleotides enhancing antigen-specific T-cell response. The invention also provides at least one RNA poly/oligonucleotide for use as a vaccine adjuvant. The RNA poly/oligonucleotides are further useful as prophylactic or therapeutic vaccines.

Furthermore, the present application provides the use of at least one RNA poly/oligonucleotide for the preparation of a pharmaceutical composition for inducing an anti-viral response, in particular, a type I IFN response, more specifically, an IFN-α response, in a vertebrate animal, in particular, a mammal. The present application further provides the use of at least one RNA poly/oligonucleotide for the preparation of a pharmaceutical composition for preventing and/or treating a disease and/or disorder in a vertebrate animal, in particular, a mammal, in medical and/or veterinary practice.

The disease or disorder is one that can be prevented or treated by type I IFN. The diseases and/or disorders include, but are not limited to, infections, tumors/cancers, and immune disorders.

Infections include, but are not limited to, viral infections, bacterial infections, anthrax, parasitic infections, fungal infections and prion infection.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In one embodiment, the infection is an upper respiratory tract infection caused by viruses and/or bacteria, in particular, flu, more specifically, bird flu.

Bacterial infections include, but are not limited to, infections by streptococci, staphylococci, *E. coli*, and pseudomonas. In one embodiment, the bacterial infection is an intracellular bacterial infection, which is an infection by an intracellular bacterium such as mycobacteria (tuberculosis), chlamydia, mycoplasma, *listeria*, and a facultative intracelluar bacterium such as *Staphylococcus aureus*.

Parasitic infections include, but are not limited to, worm infections, in particular, intestinal worm infection.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

Tumors include both, benign and malignant tumors (i.e., cancer). Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, the cancer is selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Immune disorders include, but are not limited to, allergies, autoimmune disorders, and immunodeficiencies. Allergies include, but are not limited to, respiratory allergies, contact allergies and food allergies.

Autoimmune diseases include, but are not limited to, multiple sclerosis, diabetes mellitus, arthritis (including rheumatoid arthritis, juvenile rheumatoid arthritis, osteoarthritis, psoriatic arthritis), encephalomyelitis, myasthenia gravis, systemic lupus erythematosis, autoimmune thyroiditis, dermatitis (including atopic dermatitis and eczematous dermatitis), psoriasis, Siogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

In a preferred embodiment, the immune disorder is multiple sclerosis.

In certain embodiments, the poly/oligonucleotide is used in combination with a delivery agent. In one embodiment, the delivery agent is a complexation agent, wherein the poly/oligonucleotide and the complexation agent form a complex. In another embodiment, the delivery agent is a replication-deficient virus, wherein the poly/oligonucleotide is encapsulated in the viral capsule.

In other embodiments, the poly/oligonucleotide is used without a delivery agent. In certain embodiments, the poly/oligonucleotide, with or without a delivery agent, is used in combination with one or more pharmaceutically active agents such as immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. Preferably, the pharmaceutically active agent is selected from the group consisting of an immunostimulatory agent, an anti-viral agent and an anti-tumor agent. The more than one pharmaceutically active agents may be of the same or different category.

In one embodiment, the poly/oligonucleotide, with or without a delivery agent, is used in combination with an anti-viral vaccine, an anti-bacterial vaccine, and/or an anti-tumor vaccine, wherein the vaccine can be prophylactic and/or therapeutic. The poly/oligonucleotide can serve as a vaccine adjuvant.

In one embodiment, the pharmaceutical composition is for use in combination with one or more prophylactic and/or therapeutic treatments of diseases and/or disorders such as infection, tumor, and immune disorders. The treatments may be pharmacological and/or physical (e.g., surgery, radiation).

In a further embodiment, the poly/oligonucleotide comprising at least one uridine that is not involved in base pairing, is used in combination with exogenous G nucleoside. The term "used in combination" as used herein means simultaneously or consecutively by suitable route of administration as defined herein above.

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

The present invention is illustrated by the following Examples. The Examples are for illustration purpose only and shall not be construed to limit the scope of the invention.

EXAMPLES

Materials and Methods
Reagents

The RNA oligonucleotides or oligoribonucleotides (ORNs, sequences detailed in Table 1) were obtained from Eurogentec or Biomers. The CpG-containing DNA oligonucleotides or oligodeoxyribonucleotides (ODNs) CpG-ODN 2216 and CpG-ODN 2336 were purchased from Invitrogen. Polyriboinosinic:polyribocytidilic acid (pI:C) and Homopolymers poly G/U/A was obtained from Sigma-Aldrich. ORNs were resuspended in sterile endotoxin-free DEPC-treated water (Invitrogen), and CpG-ODNs were resuspended in 0.9% NaCl aqueous solution (Braun). To prevent contamination, all oligonucleotides were stored and handled under aseptic conditions. The sequences of the oligonucleotides are listed in Table I and II. Nucleic acids were suspended in sterile endotoxin free DEPC-water (Invitrogen, Karlsruhe). Unless indicated otherwise, dsRNA oligonucleotides (ds ORNs) were generated by mixing two ssRNA oligonucleotides (ss ORNs) in a ratio of 1:1 (w/w) at a concentration of 1 µg/µl. Unless indicated otherwise, nucleic acids were hybridized at a ratio of 1:1 (w/w).

The term "ORN" and "R" are used interchangeably in the following to signify an RNA oligonucleotide. For example, R805 and ORN805 refer to the same RNA oligonucleotide.

TABLE I

|  | Sequence (5' -> 3') | SEQ ID NO: | Figure |
|---|---|---|---|
| ORN |  |  |  |
| $A_8$ | AAAAAAAA | 1 | 2 |
| $C_8$ | CCCCCCCC | 2 | 2 |
| $G_8$ | GGGGGGGG | 3 |  |
| $G_{21}$ | GGGGGGGGGGGGGGGGGGGGG | 4 | 1, 2, 4, 6 |
| $U_{21}$ | UUUUUUUUUUUUUUUUUUUUU | 5 | 3, 4 |
| $U_{21}S$ | U* U* U* U* U* U* U* U* U* U* U* U* U* U* U* U* U* U* U* U* U* | 6 | 1 |
| $A_{21}$ | AAAAAAAAAAAAAAAAAAAAA | 7 | 2 |
| $C_{21}$ | CCCCCCCCCCCCCCCCCCCCC | 8 | 2 |
|  | CCCUCC | 9 | 2 |
|  | CCCUCCC | 10 | 2 |
| R805 | CCCCUCCC | 11 | 2-6 |
|  | CCCCCUCCCC | 12 | 2 |
|  | CCCCCCUCCCCC | 13 | 2 |
|  | CCCCCCCUCCCCCCC | 14 | 2 |
|  | CCCCCCCCCUCCCCCCCCC | 15 | 2 |
|  | AAAAGAAA | 16 | 2 |
|  | AAAAAAGAAAAA | 17 | 2 |
|  | AAAAAAAGAAAAAA | 18 | 2 |

TABLE I-continued

| | Sequence (5' -> 3') | SEQ ID NO: | Figure |
|---|---|---|---|
| R1602 | AAAAAAAAGAAAAAAA | 19 | 2-4 |
| | AAAAAAAAAAGAAAAAAAAAA | 20 | 2 |
| | AAAAAGAAAAAAAAAAGAAAA | 21 | 2 |
| 9.2s | AGCUUAACCUGUCCUUCAA | 22 | 3-5 |
| R17 | GGCAUUCUUAUUCUUACGG | 23 | 3-4 |
| R1917 | GGCAUUCUUAUUCUUACGG | 24 | 4 |
| R2115 | CCCUCCCCGGGGGGGGGGGG | 25 | 4-5 |
| R2116 | GGGGGGGGGGGGGCCCUCCCC | 26 | 4 |
| R2117 | CCCUCCGGGGGGGGGGGGGG | 27 | 4 |
| R3101 | CCCUCCCCGGGGGGGGGGGGGGGGGGGGG | 28 | 4 |
| R2127 | CCCCCCCCGGGGGGGGUGGG | 29 | 5 |
| R2151 | CGCGCGCGCAGAAGCGUGCGC | 30 | 13 |
| R2152 | CGCGUGCGCAGAAGCGCGCGC | 31 | 13 |
| R2153 | CGGCUCGGCAGAAGCCGGGCC | 32 | 13 |
| R2161 | CGCCUGGGCAGAAGCCCGGGC | 33 | 14 |
| R805PTO-U | CCCC*U*CCC | 34 | 5 |
| R805 2'-O-Me-U | CCCCmUCCC | 35 | 5 |
| R805 ψ | CCCCψCCC | 36 | 5 |
| CpG-ODN | | | |
| CpG 2216 | G*G*GGGACGATCGTCG*G*G*G*G | 37 | 3, 4 |
| CpG 2336 | G*G*G*G*ACGACGTCGTGGG*G*G*G | 38 | 3 |

*phosphothioate bond

Isolation of Human PBMCs, PDCs and Human Monocytes

Human PBMCs were prepared from blood of healthy male and female donors. Fresh Buffy-Coats were obtained from the Institute of Experimental Hematology and Transfusion Medicine of the University Bonn (Bonn, Germany). PBMCs were purified by biocoll density gradient centrifugation (Biochrom AG). PDC were isolated by using the MACS CD304 (BDCA-4/Neuropilin-1)-MicroBead Kit (Miltenyi, Bergisch Gladbach). Monocytes were prepared by depleting PDC and using the Monocyte Isolation Kit II (Miltenyi). The purity of PDCs and monocytes was determined by antibody (obtained from BD Bioscience, Heidelberg and Miltenyi) staining followed by flow cytometric (FACS) analysis and was typically >90%.

Generation of FLT3-L PDCs from Mouse Bone Marrow

Cells were isolated from bone marrow of wild-type or TLR7$^{-/-}$ mice. Cells were cultured in RPMI 1640 supplemented with 10% FCS, 0.1 mM MEM non-essential amino acids, 1 mM MEM sodium pyruvate (all from Gibco), 2 mM L-glutamine (Cambrex BioWhittaker), 100 U/ml Penicillin, 100 µg/ml Streptomycin (PAA Laboratories GmbH) and 20 ng/ml FMS related tyrosine kinase 3 ligand (rFLT3-L) R&D systems. After 7 days, non-adherent cells were collected and the PDCs were isolated by MACS-separation using B220-MicroBeads (Miltenyi).

Cell Culture

Human cells were cultured in RPMI 1640 (Gibco) supplemented with 2% human serum (Cambrex, BioWhittaker), 2 mM L-glutamine (Cambrex, BioWhittaker), 100 U/ml Penicillin and 100 µg/ml Streptomycin (PAA Laboratories GmbH) in 96-well flat-bottom plates. The density of human PBMCs and human monocytes was 4×10$^5$ cells/200 µl per well, and the density of human PDC was 4×10$^4$ cells/200 µl per well. Mouse PDCs were cultured in 96-well flat-bottom plates in RPMI 1640 supplemented with 10% FCS, 0.1 mM MEM non-essential amino acids, 1 mM MEM sodium pyruvate (all from Gibco), 2 mM L-glutamine (Cambrex BioWhittaker), 100 U/ml Penicillin and 100 µg/ml Streptomycin (PAA Laboratories GmbH). The density of mouse pDC was 4×10$^4$ cells/200 µl per well.

In Vitro Cell Stimulation

Stimulations were performed in triplicate in 96-well flat-bottom plates (Nunc, Langenselbold) with a 200 µl total volume, and incubated for 20 h at 37° C., 5% CO$_2$. Unless where indicated otherwise, homopolymers, ORN or CpG-ODN were complexed to the polycation Poly-l-arginine (P4663 by Sigma-Aldrich) and used at a final concentration of 1 µg/ml. Poly I:C was transfected with TransIT-LT1 (Mirus, Madison). Mouse PDC were transfected with ORN or CpG-ODN using the Dotap liposomal transfection reagent (Roth, Karlsruhe). Human cells, were cultured in RPMI 1640 (Gibco, Karlsruhe) supplemented with 2% human serum (Cambrex BioWhittaker, New Jersey), 2 mM L-glutamine (Cambrex BioWhittaker), 100 U/ml Penicillin and 100 µg/ml Streptomycin (PAA Laboratories GmbH, Pasching). Cells were plated in 96 well plates at a density of $4 \times 10^5$ cells/200 µl for human PBMC and monocytes, and $4 \times 10^4$ cells/200 µl for PDC. Mouse PDC were cultured in RPMI 1640 supplemented with 10% FCS, 0.1 mM MEM non-essential amino acids, 1 mM MEM sodium pyruvate (all from Gibco), 2 mM L-glutamine (Cambrex BioWhittaker), 100 U/ml Penicillin, 100 µg/ml Streptomycin (PAA Laboratories GmbH) at a density of $4 \times 10^4$ cells/200 µl. Supernatants were removed and assayed for cytokine production.

In Vivo Stimulation

Wild-type mice were injected i.v. with 25 µg ORN formulated with 125 µg Dotap. Mice were bled 3 h, 5 h and 8 h post-injection via the tail vein. Serum was purified and the IFN-α level was measured.

Detection of Cytokine

Supernatants from human or mouse cells were harvested 20 h after stimulation. If not used immediately, supernatants were frozen at −20° C. until used. IFN-α and/or IL-12p70 were analysed in the supernatant by ELISA. The human IFN-α ELISA was purchased from Bender MedSystems (Vienna), and the human IL-12p70 ELISA from BD Biosciences. Murine IFN-α in the supernatants of stimulated mouse cells or in mice sera was measured by the mouse IFN-α ELISA Kit (PBL Biomedical Laboratories).

Fluorescence Microscopy

Uptake of fluorescence labelled RNA by PDC was analysed using a Observer D1 fluorescence microscope (Zeiss, Göttingen). Cells were incubated for 2.5 h with Cy3-labelled ORN R805 6 µg/ml either alone or together with 6 µg/ml pA or pG. PDC were then stained with anti-BDCA-1 (CD303, Miltenyi) followed by the secondary antibody goat anti mouse Alexa 488 (Invitrogen). Nuclei were visualized using Hoechst 33342 (Hoechst, Frankfurt).

Statistics

Results are expressed as mean±standard error of mean (s.e.m.). Group comparisons were carried out using a two-tailed Student's t-test with an expected unequal variance.

Example 1

Poly Uridine (polyU, pU)-Stimulated IFN-α Induction is Enhanced by the Formation of Double Strands Via G:U Base Pairing Human peripheral blood mononuclear cells (PBMCs) and purified PDCs were stimulated with pU, pG, either in the form of an ssRNA or dsRNA The levels of IFN-α induced by RNA with uridine repeats of varying lengths were compared to those obtained by other polyribonucleotides, either in the form of single stranded (ss) or as double stranded (ds) RNA. Among the ssRNAs, polyU was found to stimulate IFN-α production from both human PBMCs (FIG. 1A) and human PDCs (FIG. 1B), whereas polyguanosine (pG), poly adenosine (pA), poly cytidine (pC) were inactive (data not shown). The formation of dsRNA between pU and pA greatly reduced or almost completely abolished the IFN-α-inducing activity of single-stranded pU. In stark contrast, the formation of dsRNA between pU and pG significantly and consistently enhanced the IFN-α-inducing activity of single-stranded pU, although the relative number of U within pU:pG was reduced by 50% compared to pU alone (FIG. 1B). Similar results were obtained when oligo uridine (oligoU) 21 nucleotides in length ($U_{21}$) and oligo guanosine (oligoG) ($G_{21}$) were tested (FIGS. 1C & D).

These findings are very surprising since it has long been established that TLR7 recognizes single-stranded RNA.

Example 2

The Presence of a Single G:U Base Pair in RNA Stem Structure is Sufficient to Induce High Levels of type I IFN To decipher the basis for the increase in IFN-α-inducing activity observed with pU:pG, 21mer ORNs were designed by the inventors comprising A's and one or two G(s). As observed before, the pairing with oligo A 21 nucleotides in length ($A_{21}$) led to a reduction in the IFN-α-inducing activity of pU and the pairing with oligo G 21 nucleotides in length ($G_{21}$) led to an increase in the IFN-α-inducing activity of pU, further supporting a contribution of G·U base pairs. Surprisingly, when a 21mer ORN containing 20 A's and 1 G or 19 A's and 2 G's were paired with pU, the IFN-α-inducing activity of the dsRNA was significantly higher than that of single-stranded pU, and was comparable or even higher than the partially double-stranded $G_{21}$:pU (FIG. 2A). Of note, none of the 21mers tested, on its own, was able to induce IFN-α. This observation shows that G·U base pairs represent the molecular structure that is recognized by TLR7.

Subsequently, we designed RNA oligonucleotides of different lengths consisting of A's around a central G, and tested whether the number of neighbouring base pairs influenced the IFN-α-inducing activity of the G:U base pair. We found that, when paired with polyU, a range of ORNs, having 7-8 A's flanking the central G, showed IFN-α-inducing activity (FIG. 2B). The G·U containing dsRNA pU+R1602 was selected for subsequent experiments (FIG. 2A).

While polyU on its own was able to induce type I IFN in PBMCs, polyG was inactive, but may become stimulatory when hybridized to ORN that introduce G·U base pairs. (FIG. 1A). It was tested whether G:U base pairing would render the otherwise inactive polyG active in inducing IFN-α. ORNs consisting of two stretches of C's around a central U were designed by the inventors. Surprisingly, the highest IFN-a-inducing activity was observed when pG was paired with ORNs containing 2-5 C's flanking the central G; any further increase in the number of flanking C's resulted in a drastic decrease and eventual abolishment of the IFN-α-inducing activity of the partially double-stranded RNA (FIG. 2C). From these data, the inventors hypothesized that the IFN-α-inducing activity of a partially double-stranded RNA is determined by the stability of the double-stranded RNA structures surrounding the G:U base pair, with G:C base pair providing three hydrogen bonds, and U:A base pair providing two hydrogen bonds. Both, too low and too high, stability comprise or eliminate the IFN-α-inducing activity of the partially double-stranded RNA oligonucleotide. To confirm our hypothesis, the software DNamelt (www.bioinfo.rpi.edu/applications/hybrid1) assigned similar stability to the double-stranded portion of the two most active partially double-stranded RNAs tested, pU+ORN1602 (AAAAAAAAGAAAAAAA) (SEQ ID NO: 19) and pG+ORN805 (CCCCUCCC) (data not shown).

Furthermore, the IFN-α-inducing activity of partially double stranded RNAs formed by pG and ORN805 (CCCCUCCC) mixed at different weight ratios was tested. When pG and ORN805 were mixed at a ratio of 1:1 (w/w), it was expected that the resulting RNA would be mostly double-stranded. A step-wise reduction in the amount of ORN805 would be expected to result in a step-wise increase in abundance of single-stranded structures. We found that maximal IFN-α-inducing activity was maintained up to a pG:ORN805 ratio of 20:1 (w/w). IFN-α-inducing activity was maintained down to a ratio of 100:1 which corresponds to one G·U base pair in 80 to 100 bases of RNA. This indicates that few short RNA stems (8mer) containing very few G·U wobble base pairs within long ssRNA are sufficient for detection by TLR7 in PDC.

Taken together, these results suggest that ssRNAs comprising short double-stranded structures containing G:U base pairs, rather than dsRNAs, are capable of inducing the production of type I IFN from human PBMCs and PDCs.

Example 3

Mechanism of G:U Base Pair-mediated Stimulation

Type I IFN production in response to ssRNA oligonucleotides in both, human and mouse, PDCs has been shown to depend on TLR7 [7]. Toll-like receptors able to recognize nucleic acid ligands are located in the endosomal compartment and their activation can be blocked by chloroquine, which inhibits the acidification of the endosomes. In contrast, the recognition of nucleic acids by cytosolic helicases such as RIG-I (retinoic inducible gene I) and MDA-5 (melanoma differentiation antigen 5) are not sensitive to chloroquine (Gitlin L et al, 2006).

To investigate whether the recognition of RNA containing G:U base pairs was TLR-dependent, human PBMCs that were pre-incubated with an increasing amount of chloroquine were stimulated. As expected, TLR9-dependent recognition of CpG ODN was chloroquine-sensitive, whereas the MDA-5-mediated recognition of poly(I:C) (pI:C) was not. It was found that IFN-α production induced by both polyU:R1602 and polyG:R805 were sensitive to chloroquine (FIG. 3A), indicating that their recognition of RNAs containing G·U base pairs, i.e. pU+R1602 or pG+R805 was mediated by an endosomal TLR.

Figure 2:
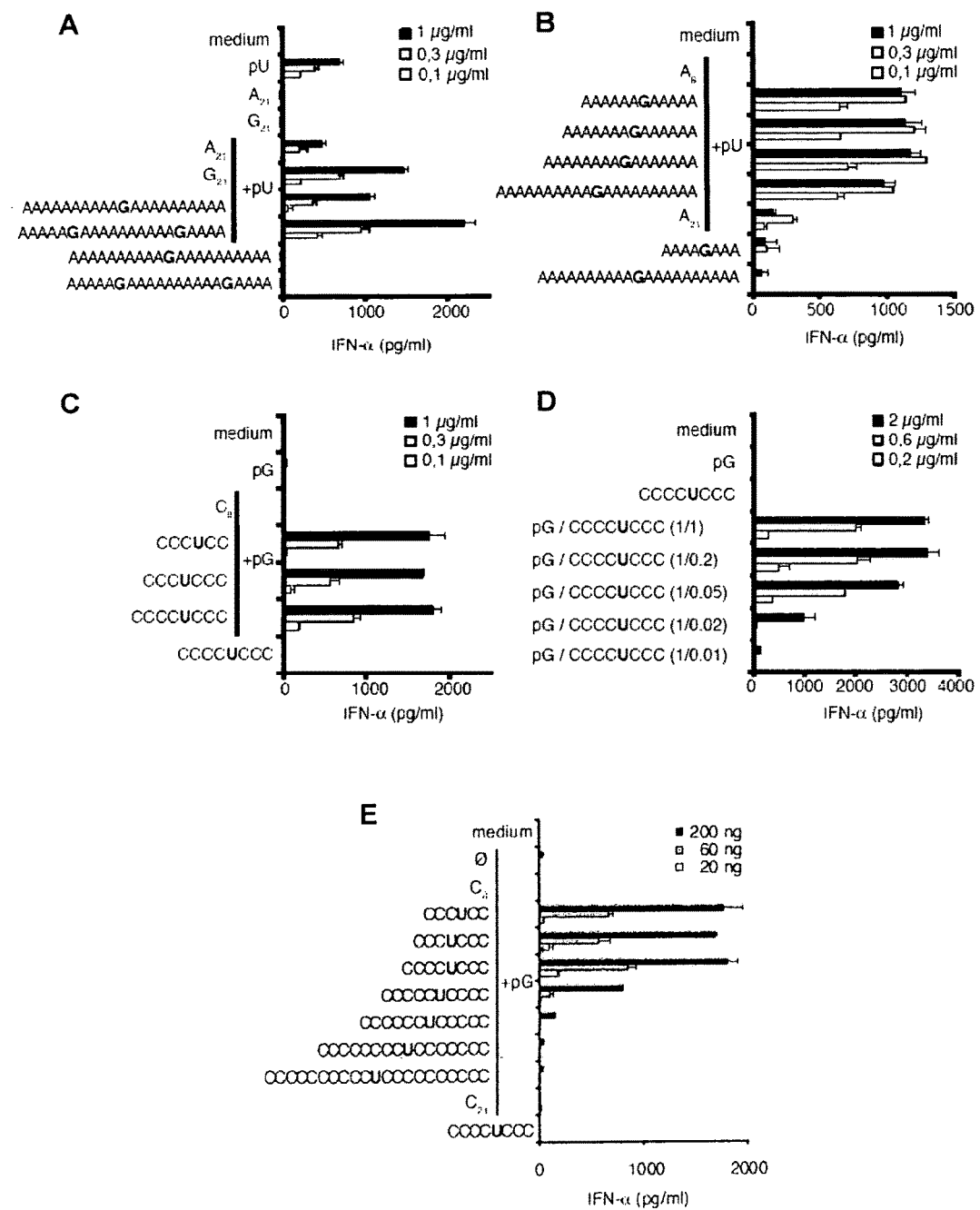
FIG. 2: RNA stem structures containing a single G:U base pair are strong inducers of type I IFN. (A-C, E) Human PBMC were stimulated with either 1 µg/ml, 0.3 µg/ml or 0.1 µg/ml or (A-C) or 200 ng, 60 ng or 20 ng RNA (E) complexed with Poly-L-Arginine. The cells were stimulated with either ssRNA or dsRNA. dsRNAs were prepared by hybridizing various short ssRNA (trimer to 21mer, ORNs) to pU (A,B) or pG (C) in equal quantities (w/w). (D) 8mer ssRNA (CCCCUCCC) was titrated to a constant amount of pG (ratio 1/1, 1/0.2, 1/0.05, 1/0.02, 1/0.01) as indicated in the figure. Human PBMC were stimulated with 2 µg/ml, 0.6 µg/ml or 0.2 µg/ml dsRNA and as control with pG or R805 alone. 20 h after stimulation, cell culture supernatants were assed for IFN-α by ELISA. Data shown are representative for 4 independent experiments.
Figure 3:
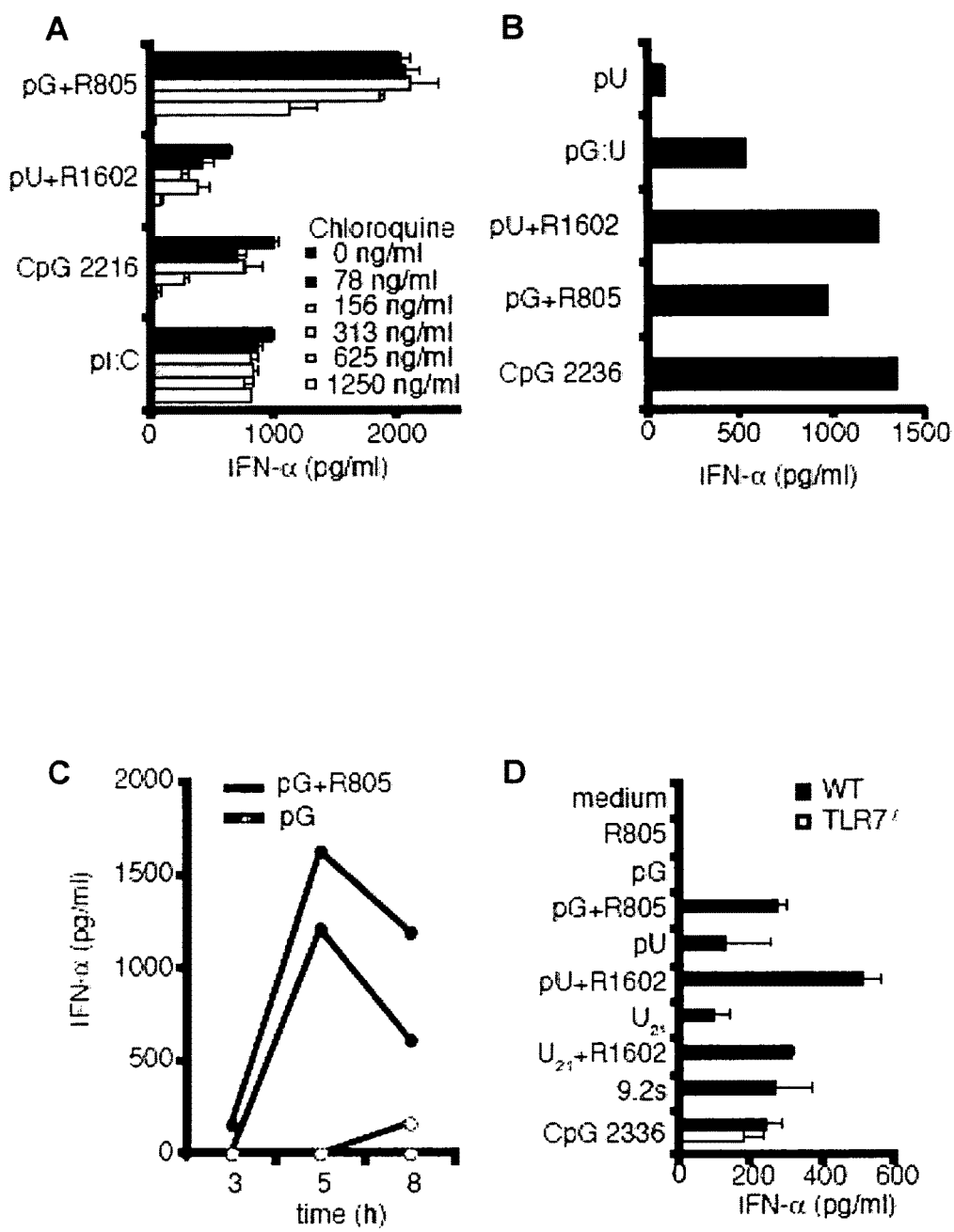
FIG. 3: Recognition of G:U base pairs is mediated by TLR7. (A) human PBMCs were pre-incubated for 30 min with different concentrations of chloroquine as indicated in the figure. pG+R805 and pU+1602 were complexed with Poly-L-Arginine to stimulate the cells. As control, PBMC were transfected with pI:C or stimulated with CpG-DNA 2216. (B) Induction of IFN-α in murine PDC derived from bone marrow cultures in vitro by pG:pU and pG+R805. Addition of R1602 strongly enhanced IFN-α levels. (C) Wild-type mice were injected i.v. with 25 µg pG, pG+R805, in complex with Dotap. Serum samples were taken 3, 5 and 8 h after stimulation and serum IFN-α was analyzed by ELISA. The lines show cytokine kinetics in individual mice(D) IFN-α-inducing activity of RNAs CpG oligonucleotide 2336, pU, oligoU ($U_{21}$) and G:U base pair-containing RNAs (pG+ORN805 and pU+ORN1602) in FLT3-L PDCs from wild-type (WT) and TLR7$^{-/-}$ mice that were stimulated in vitro with ssRNA or dsRNA complexed to Dotap. 20 h after stimulation, cell culture supernatants were assed for IFN-α by ELISA. CpG-DNA 2336 was used as positive control in a concentration of 3 µg/ml

Subsequently, mouse gene knock-out models were prepared to confirm the requirement of TLR7; consistent with the results in human immune cells (FIGS. 1 and 2). Next, pG:pU and pG+R805 were used to induce IFN-α in murine PDC derived from bone marrow cultures in vitro (FIG. 3B). Addition of R1602 strongly enhanced IFN-α levels. Injection of G·U containing RNAs in complex with Dotap in mice in vivo induced a systemic type I IFN response (FIG. 3C). Finally, using FLT3-L PDCs from wild-type (WT) and TLR7$^{-/-}$ mice and stimulated them in vitro with ssRNA or dsRNA complexed to Dotap, it was found that IFN-α-inducing activity of RNAs that contained G·U base pairs required TLR7 while this was not the case for the CpG oligonucleotide 2336 (positive control), which is recognized by TLR9. Whereas pU, oligoU ($U_{21}$) and G:U base pair-containing RNAs (pG+ORN805 and pU+ORN1602) induced IFN-α production in WT PDCs, they failed to do so in TLR7$^{-/-}$ PDCs (FIG. 3D).

These results indicate that IFN-α production induced by G:U base pair-containing RNA is mediated by TLR7. Furthermore, these results confirm the notion that a single G:U base pair is sufficient to activate TLR7 (FIG. 3C, U21+ ORN1602).

Example 4

Selective Activation of Human PDC by RNA Containing G:U Base Pairs

Figure 4:
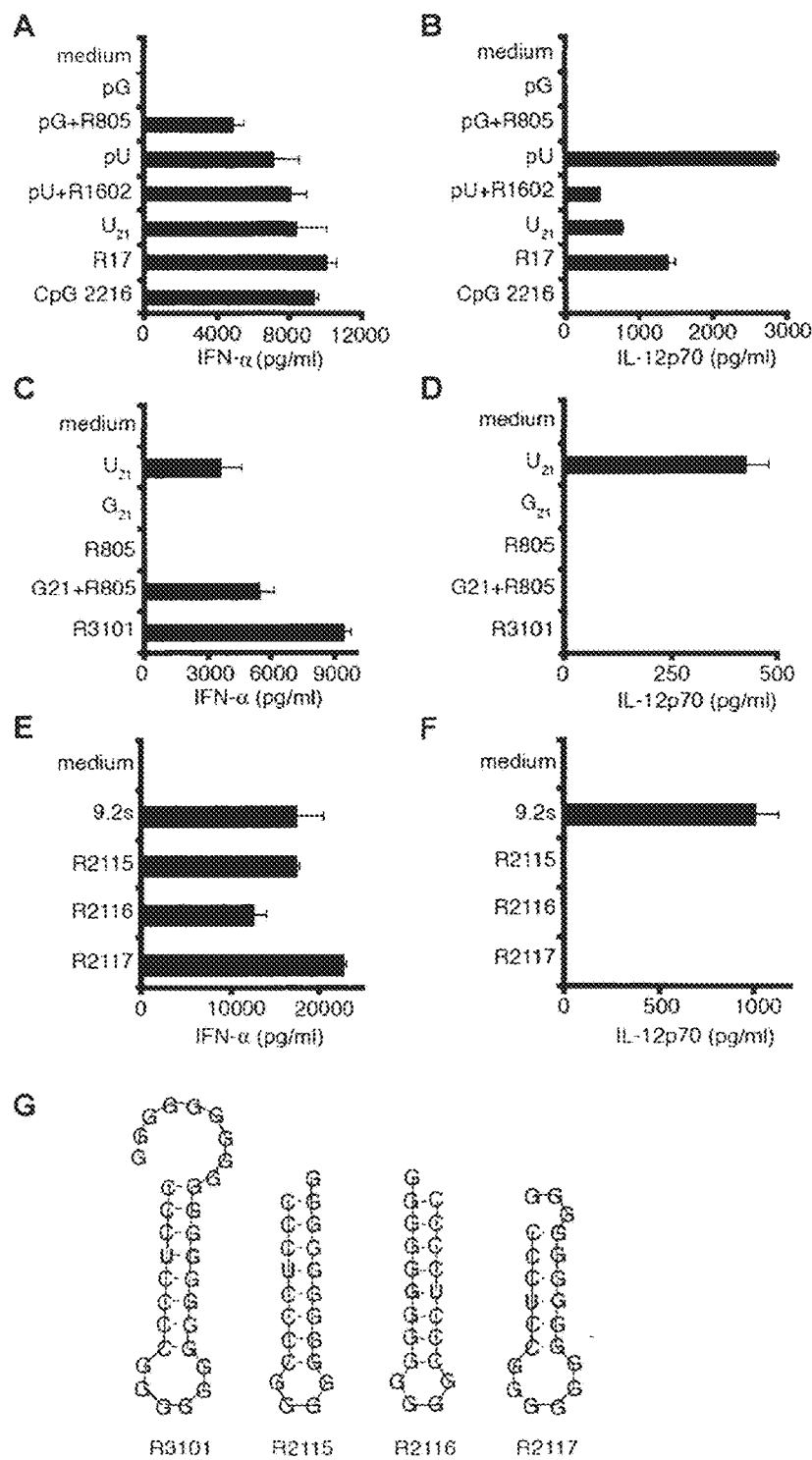
FIG. 4: G:U base pairs selectively activate TLR7. Human PDC (A, C, E) or human monocytes (B, D, F) were stimulated with ssRNA or dsRNA complexed with Poly-L-Arginine. Supernatants were harvested 20 h after stimulation and IFN-α was analyzed by ELISA. Figure (G) shows the preferred secondary structure of ORNs containing a G·U base pair.

Most of the published RNA ligands activate both TLR7 and TLR8 As a result, stimulation of PBMCs with these RNA ligands leads to TLR7-dependent production of IFN-α in PDCs as well as TLR8-dependent production of IL-12 mostly in monocytes (review Bekeredjan-Ding et al, 2005 and 2006). Therefore, the ability of different RNA molecules to induce IFN-α in PDC and IL-12 in monocytes (FIGS. 4A and B) was compared. The cytokine production in human PDCs and monocytes in response to a published RNA ligand (9.2s) and RNA containing G:U base pairs was measured. It was found that, while pU, pU+R1602, U21 and R17 (identical to R1917) induced both, IFN-α in PDC and IL-12 in monocytes, CpG ODN, pG+R805 selectively activated PDC but not monocytes, indicating that pG+R805 exclusively activates TLR7 but not TLR8. TLR7 selectivity was seen for all duplex forming RNA molecules that contain at least one single G·U base pair and in which the corresponding single strands did not activate PDC or monocytes (FIG. 4). Selective activation of PDC was also achieved with single strand ORN (R3101, R2115, R2116, R2117) that form a stem loop structure containing at least one single G·U wobble base pair (FIG. 4C, D, E, F, G). In this setup, a G·U containing stem structure of 6 bp was sufficient to elicit a potent IFN-α response without inducing IL-12p70 in monocytes (FIG. 4E, F), a further indication that the G·U base pair is selectively recognized by human TLR7 but not by TLR8 (FIG. 4F).

Figure 5:
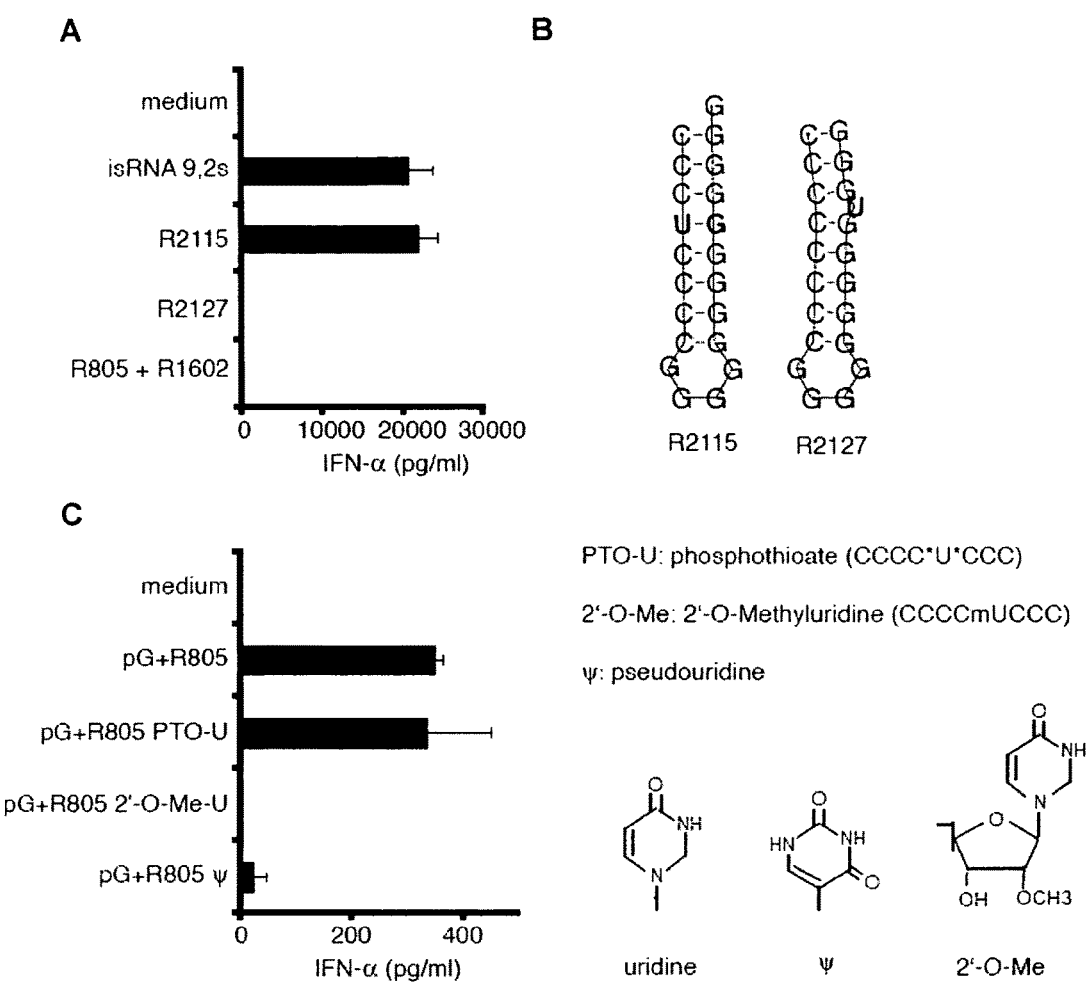
FIG. 5: RNAs containing G and U that are unable to form a G·U base pair are inert: Human PDCs were stimulated with RNA complexed to Poly-l-Arginine. After 20 h, IFN-α was measured in the supernatants by ELISA. Data shown are representative of 3 independent experiments. (B) Secondary structure of oligonucleotides used in (A). It is apparent that even with the overall base composition conserved, oligonucleotides are inert when a G·U base pair cannot form. (C) RNA modifications that affect the integrity of the G·U base pair interfere with stimulatory activity. Human PDC were stimulated with RNA pG+R805 containing one single uridine (R805), phosphothioated-uridine (R805PTO-U), 2'-O-methyluridine (R805 2'-O-Me) or pseudouridine (R805 y) in complex with Poly-L-Arginine. After 20 h of culture, IFN-a was measured in the supernatants by ELISA. Data shown are representative of 3 independent experiments. Modifications of the Uridine in the G·U base pair abrogate activity. Shown are modifications to Pseudouridine and to 2-O-Methyl-Uridine. In contrast, phosphorthioate modifications that affect the phosphodiester linkage to neighboring bases is tolerated.

ORNs that contained a single uridine, form a duplex or a stem loop structure but do not form a G·U wobble base pair did not induce IFN-α, confirming the strict G·U wobble base pair specificity of selective TLR7 ligands (FIG. 5A, B). Moreover, chemical modification of the uridine within R805 to pseudouridine or 2'-O-Me-Uridine largely abrogated activity of the complex with pG (FIG. 5C).

These data suggest that TLR7 and 8 recognize different molecular motifs and it is possible to design TLR7-specific RNA ligands.

Example 5

RNA Containing G:U Base Pairs Stimulates Human PDC in the Absence of Transfection Reagents Stimulation of TLR7 by RNA oligonucleotides has been shown to depend on the use of complexation or transfection reagents, which facilitate the cellular uptake and delivery of RNA ligands to TLR7 which is confined to the endosomal compartment. In addition, complexation with poly-cations protects RNA from degradation (review Diebold S S et al, 2004, Heil et al, 2004 and Heil et al 2003). Naked RNA is inherently unstable because its phosphodiester backbone is susceptible to both alkaline hydrolysis and degradation by ubiquitous RNases. Because most cellular RNases preferentially degrade ssRNA, it was tested whether stem structures containing a G·U base pair were able to stimulate PDC also in the absence of complexation reagents. Surprisingly, "naked" polyG+R805 not complexed with any complexation or transfection agent was not only active in inducing high levels of type I IFN, it was as active as polyG+R805 complexed with poly L-arginine (FIG. 6A) using the same quantities. Using R805 hybridized to short synthetic pG ORN (42mer, 21mer, 8mer) it was observed that that ability to induce IFN-α correlated with overall RNA length (FIG.

Figure 6:
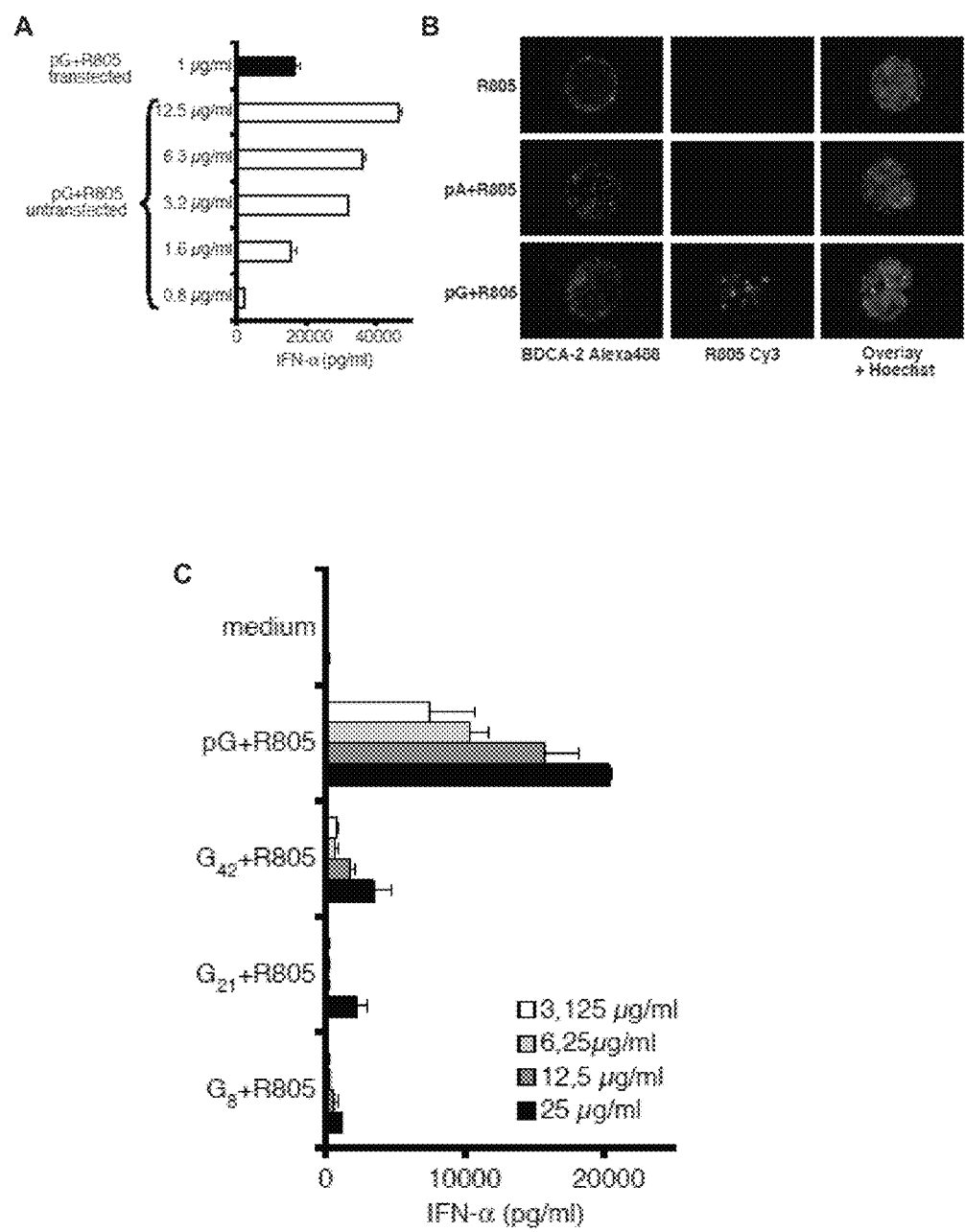
FIG. 6: G:U base pair forming complexes comprising polyG and R805 are able to activate human PDCs without transfection agents. (A) Human PDCs were stimulated with pG+R805 either complexed with Poly-L-Arginine (black bar) or without complexation (white bar) in the indicated amount. 20 h after stimulation, cell culture supernatants were assed for IFN-α by ELISA. Data shown are representative of 5 independent experiments. (B) shows the uptake of fluorescent R805 alone, together with polyA, or together with pG in human PDCs incubated with fluorescent R805 in the culture supernatant. (C) Human PDCs were isolated from Buffy Coats and stimulated with G·U base pair containing RNA produced by R805 hybridized to pG in varying lengths (pG, $G_{42}$, $G_{21}$, $G_8$). RNA was given into the supernatant of PDCs in concentrations of 25 µg/ml, 12.5 µg/ml, 6.25 µg/ml or 3.125 µg/ml. After 20 h, IFN-α was measured in the supernatants. This shows that oligo G strands (in particular G42) paired with R805 can be active without added transfection reagent, but the activity is much reduced compared to pG.

6C). In order to test whether the pG polymer indeed facilitated the uptake of hybridized ORN R805, human PDC was incubated with fluorescent R805 in the culture supernatant. It was found that PDC did not take up any R805 by itself, or together with poly A (FIG. 6B). In contrast, when R805 was added together with pG, it was readily taken up by all PDC in the sample. To our knowledge, polyG+R805 is the first example of a phosphodiester RNA, which is able to stimulate TLR7 without complex formation with a transfection reagent.

Fluorescence microscopy indicates that, indeed, polyG+R805 entered the endosomal compartments of monocytes without the aid of any complexation agent (FIG. 6B).

Example 6

Figure 7:
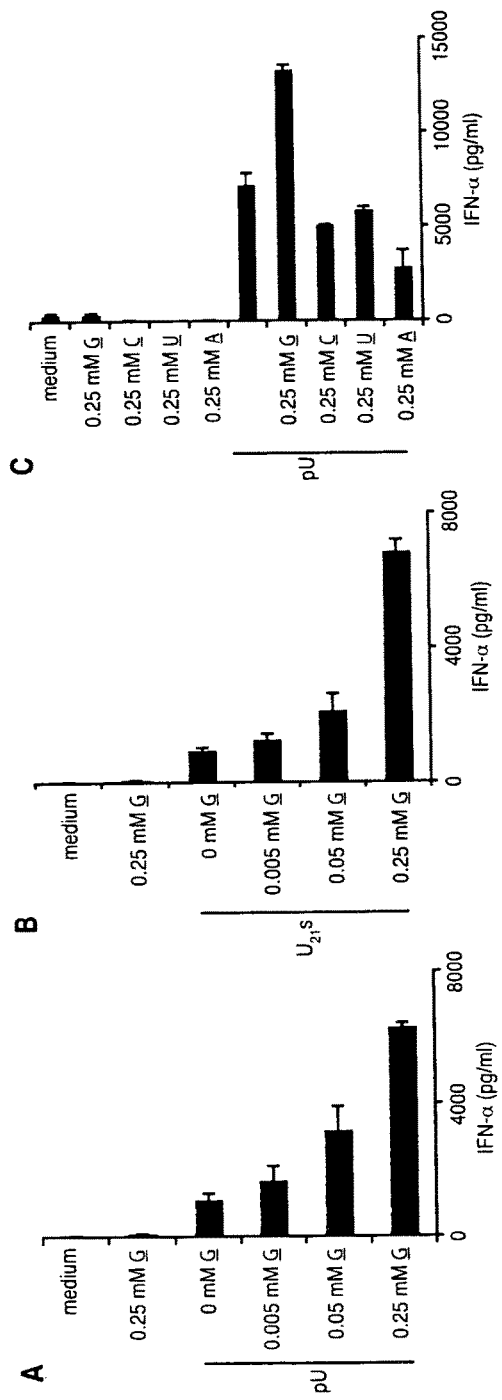
FIG. 7: Addition of guanosine nucleosides strongly enhances the type I IFN response to poly uridine RNA. Human PDC were stimulated with pU (A, C) or with $U_{21}$s (B) complexed to Poly-L-Arginine. (A, B) At the same time guanosine-nucleosides (G) in different concentrations (0.005 mM, 0.05 mM or 0.25 mM) were added to stimulated or untreated PDCs. (C) Different nucleosides (G, cytidine (C), uridine (U) or adenosine (A)) were added in a concentration of 0.25 mM to stimulated or untreated PDCs. After 20 h, cell culture supernatants were assessed for IFN-a by ELISA. Data shown are representative of 3 independent experiments.
Figure 8:
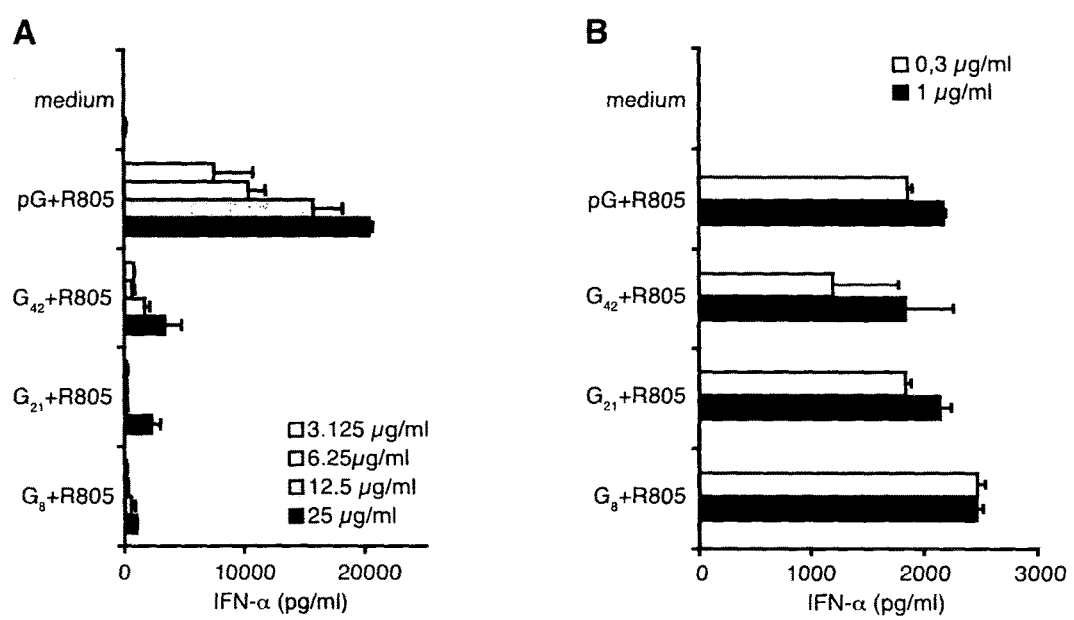
FIG. 8: The length of the RNA strand influences the stimulatory activity of untransfected, but not of transfected G·U base pair containing RNA. Human PDC were isolated from Buffy Coats and stimulated with G·U base pair containing RNA produced by R805 hybridized to pG in varying lengths (pG, $G_{42}$, $G_{21}$, $G_8$). (A) RNA was given into the supernatant of PDC in concentrations of 25 µg/ml, 12.5 µg/ml, 6.25 µg/ml or 3.125 µg/ml. (B) RNA was complexed to Poly-l-Arginin and complexes were added into the supernatants in different concentrations (0.3 µg/ml or 1 µg/ml). (A,B) After 20 h, IFN-a was measured in the supernatants. Data shown are representative of 2 independent experiments.
Figure 9:
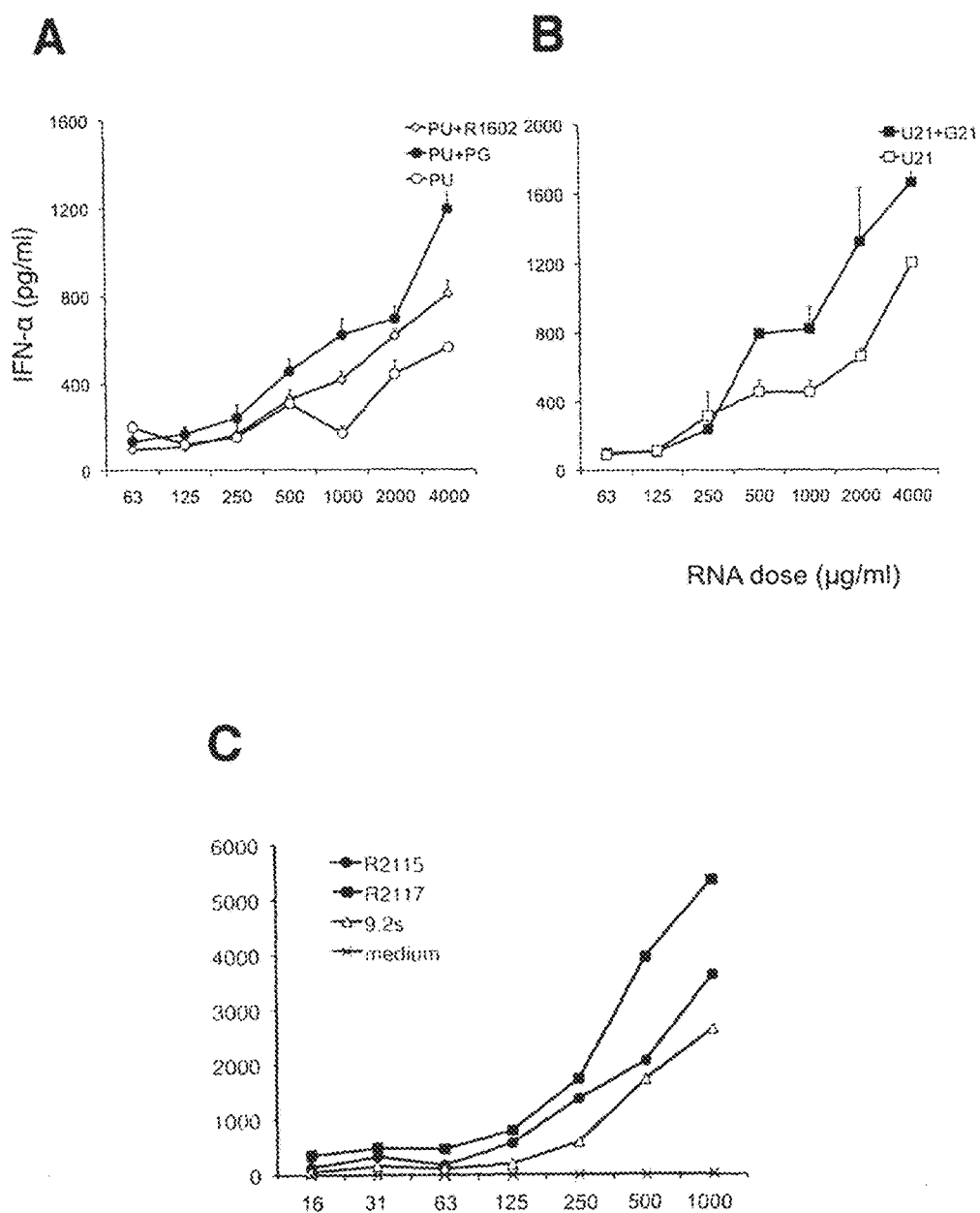
FIG. 9: Preferential recognition of G·U base pairs is evident over a wide range of doses and in differing RNA contexts. PBMC were isolated from Buffy coats and stimulated with varying concentrations of RNA complexed to Poly-l-Arginin. After 20 h IFN-a was measured in the supernatants. (A) pU compared to pU+pG and pU+R1602 (B) U21 compared to U21+G21 (C) 9.2s RNA compared to R2115 and R2117 hairpins.
Figure 10:
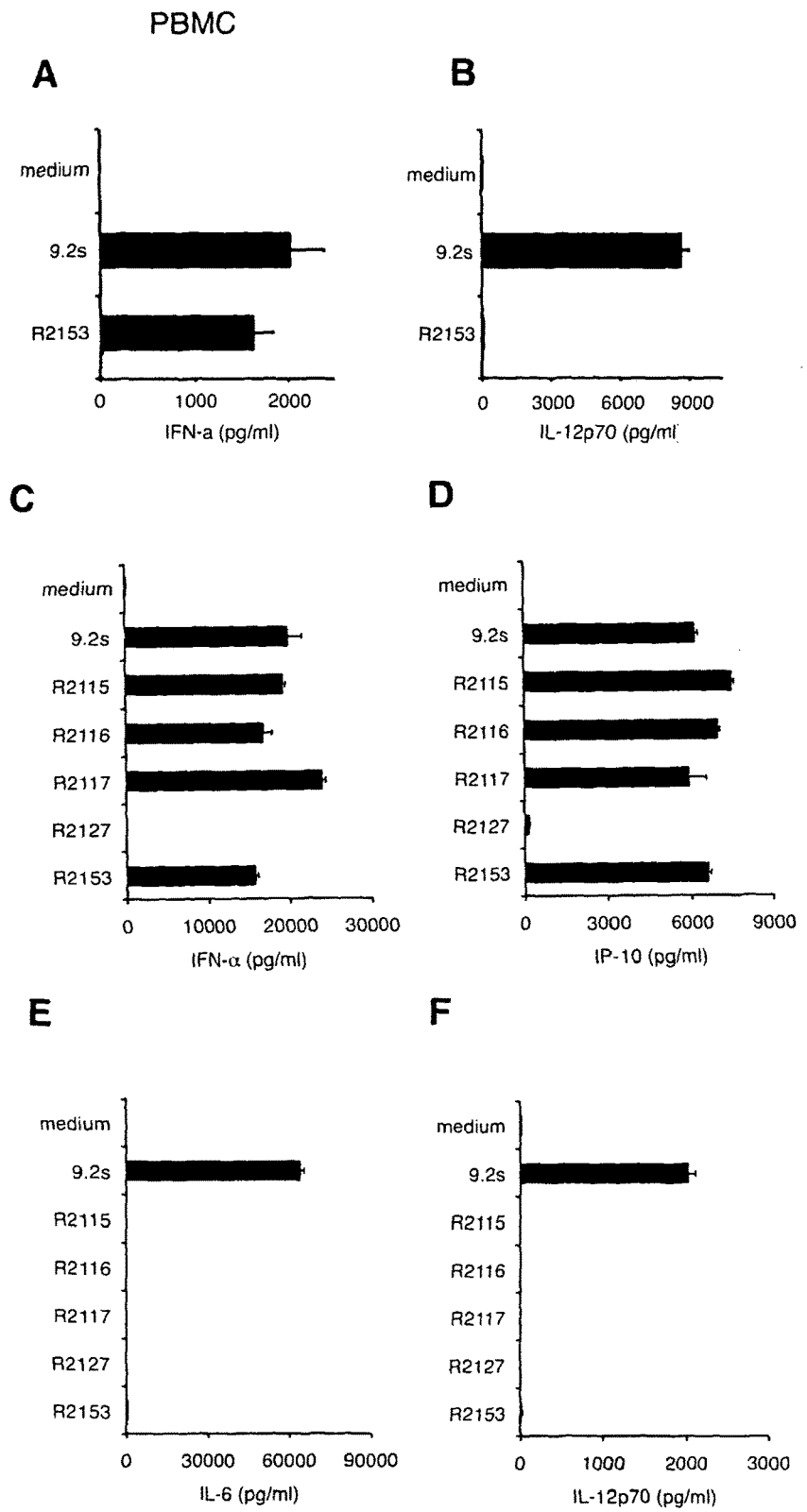
FIG. 10: GU base pairs containing RNA specifically induces IFN-a and IP-10 and not proinflammatory cyokines. PBMC were isolated from Buffy coats and stimulated with 1 µg/ml RNA containing GU base pairs. As positive control, the TLR7/8 is RNA 9.2s and as negative control RNA R2127 was used. RNAs were complexed to Poly-l-Arginine and added to the supernatants. After 20 h, cytokines ((A,C) IFN-a, (B,F) IL-12p70, (D) IP-10 and (E) IL-6 were measured by ELISA.
Figure 11:
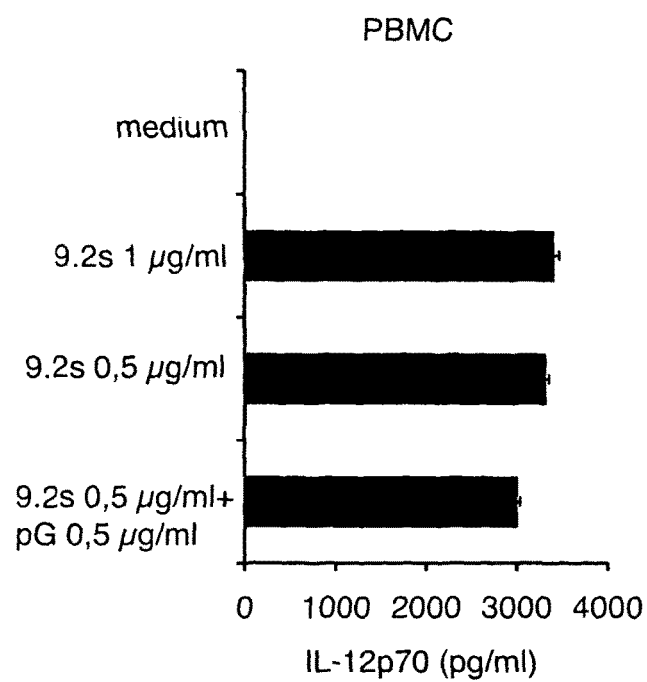
FIG. 11: The presence of pG does not per se impair TLR8 mediated recognition of RNA. PBMC were isolated from Buffy coats and stimulated with either is RNA 9.2s alone (1 µg/ml or 0.5 µg/ml) or is RNA 9.2s in presence of pG (0.5 µg/ml) 9.2s RNA and 0.5 µg/ml pG). is RNA 9.2s and pG were mixed before complexation to Poly-l-Arginine. After 20 h IL-12 p70 was measured in the supernatants.
Figure 12:
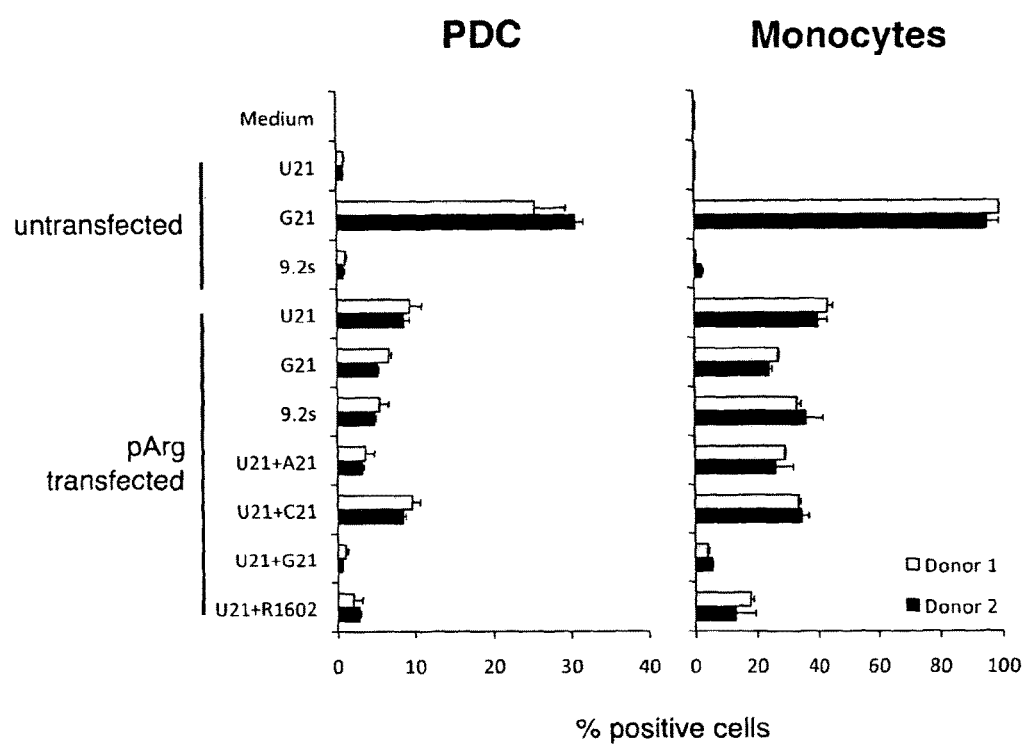
FIG. 12: Enhanced stimulation by RNAs containing G·U base pairs is not mediated by preferential uptake of RNA containing multiple guanosines. In contrast to other RNA oligonucleotides, untransfected G21 is readily taken up by PDC and monocytes. However, upon complexation with Poly-l-Arginine (pArg) all forms of RNA are taken up equally well. Moreover, while constituting the strongest immune stimulus (Figure S5) uptake of fluorescent U21 was rather reduced when hybridized to G21. Cy3 fluorescence labeled RNAs were either given untransfected or in complex with to PBMC, and incubated for 1 h. Subsequently PBMC were washed and stained for cytometric analysis. Cells that took up fluorescent RNA are shown as % positive PDC (BDCA-2$^+$) and Monocytes (CD14$^+$). Data shown is representative of three independent experiments.
Figure 13:
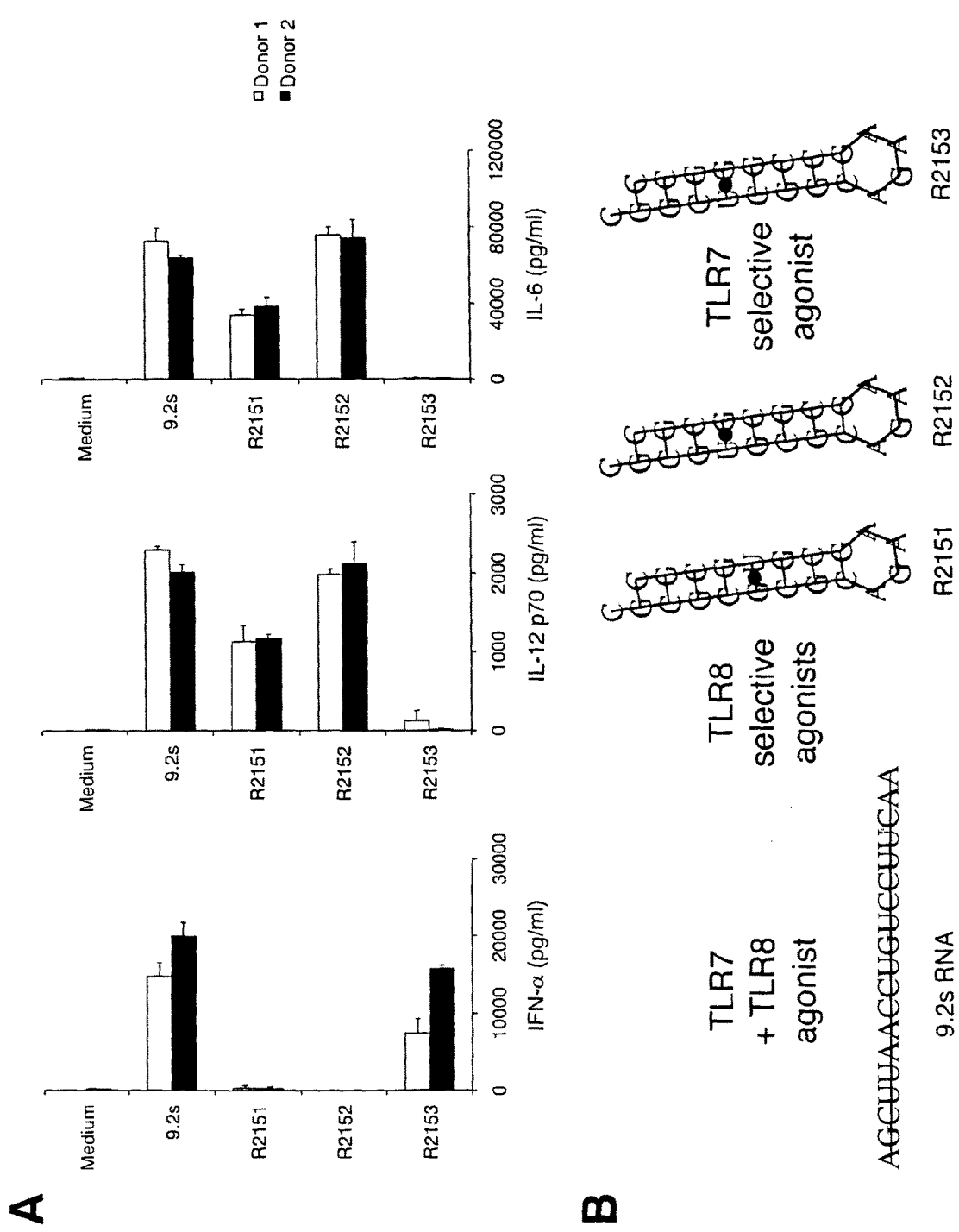
FIG. 13: Evidence that some RNA hairpins containing G·U base pairs act as selective TLR8 agonists. (A) PBMC were isolated from Buffy coats and stimulated with the RNAs shown in (B) in complex with Poly-l-Arginine. After 20 h IFN-a, IL-12 p70 and IL-6 were measured in the supernatants by cytokine Elisa. R2151 and R2152 are examples for selective TLR8 agonists.
Figure 14:
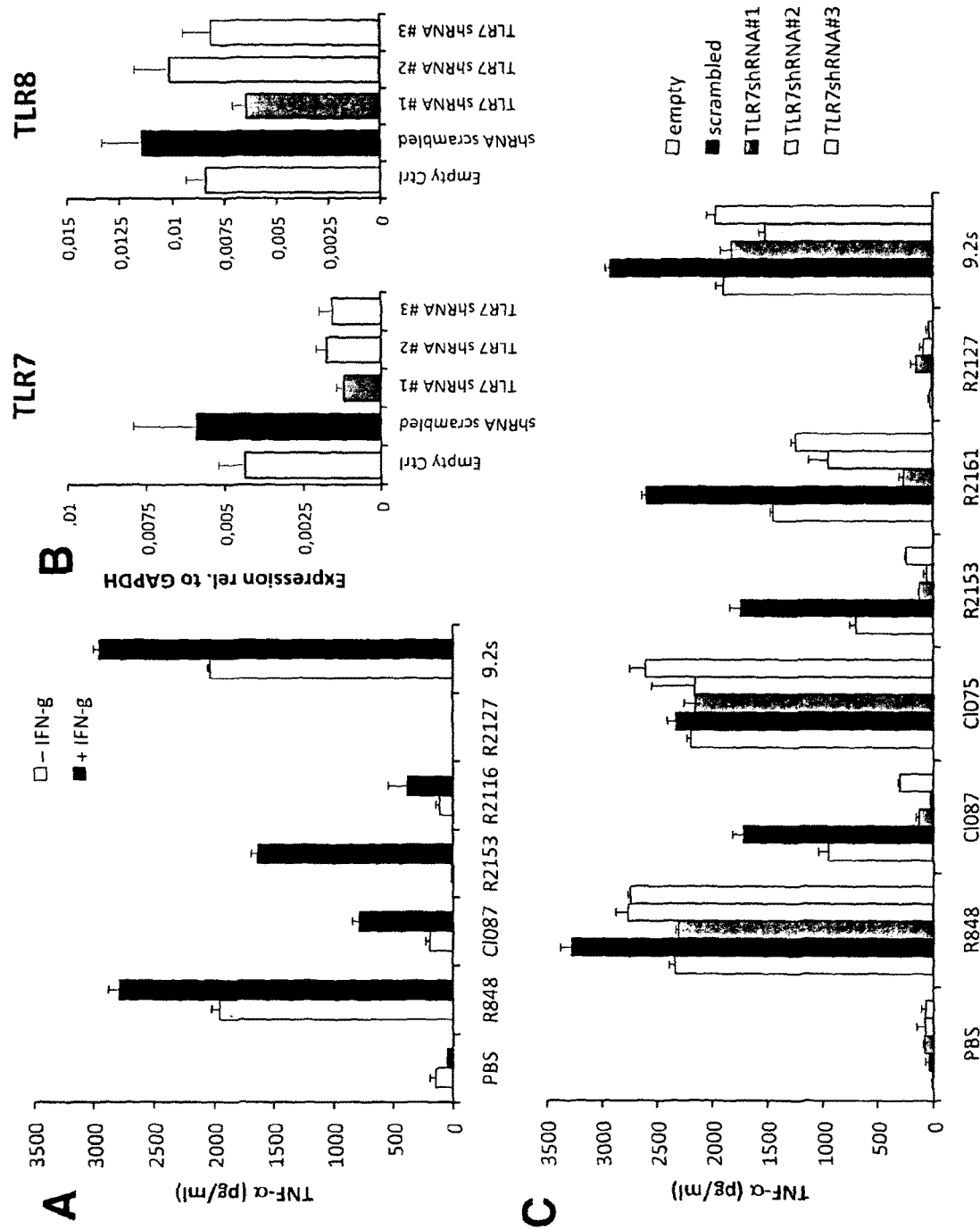
FIG. 14: In cells that express both functional TLR7 and TLR8 RNAs containing G·U wobble base pairs retain TLR7 selective activity. PMA activated THP-1 cells express TLR8, and upon stimulation with IFN-g (100 U/ml) also upregulate functional TLR7. (A) THP-1 cells were stimulated with the small molecule agonists R848 (TLR7/8 agonist) Cl087 (TLR7 agonist), or RNAs R2153, R2116 (TLR7 agonists) R2127 (inert), and 9.2s (TLR7/8 agonist). After 20 h TNF-a was measured in the culture supernatant by ELISA. (B) Knock-down of TLR7 using 3 different lentiviral shRNA constructs in PMA/IFN-g treated THP-1 cells represses TLR7 but not TLR8 mRNA. Lentiviral vectors without (empty) or with nonsense shRNA (scrambled) were used as negative controls. (C) THP-1 cells treated as in described in (B) were stimulated with small molecule agonists (R848, Cl087 and Cl075[TLR8 agonist]), or the indicated RNAs in complex with Poly-l-Arginine. After 20 h TNF-a was measured in the culture supernatant by ELISA. Data shown are representative of 2 (A) or 3 (B, C) independent experiments.

Addition of Guanosine Nucleosides Strongly Enhances the type I IFN Response to Poly Uridine RNA Human PDC were isolated from PBMC by MACS enrichment using BDCA-4 Microbeads. 40.000 PDC per well of a 96 well plate were stimulated with 200 ng pU (A, C) or with U21s (B) complexed to Poly-L-Arginine. (A, B) At the same time guanosine-nucleosides (G) in different concentrations (0.005 mM, 0.05 mM or 0.25 mM) were added to stimulated or untreated PDCs. (C) Different nucleosides (G, cytidine (C), uridine (U) or adenosine (A)) were added in a concentration of 0.25 mM to stimulated or untreated PDCs. All Nucleosides used were from Sigma-Aldrich (A 9251 Adenosine; C 9505 Cytidine; G 6752 Guanosine; U 3750 Uridine) After 20 h, cell culture supernatants were assessed for IFN-a by ELISA. Data shown are representative of 3 independent experiments. Given that high concentrations of a combination of G and U nucleosides but not the single nucleosides were reported to stimulate cytokine release in PBMC (Heil et al. 2004), and the guanosine analogue loxoribine is a known TLR7 specific stimulus (Heil et al. 2003), we next examined whether the IFN-α inducing activity of poly uridines (pU, U21s) is influenced by the addition of monomeric nucleosides. The addition of the nucleoside guanosine dose dependently increased the ability of pU and U21s to induce IFN-α in PDC (FIGS. 7A and B). No increased activity of pU or U21s was seen for the other three nucleosides cytidine, guanosine and adenosine (FIG. 7C).

Together these results demonstrate that base pairing with guanosine enhances the activity of uridine to activate TLR7 in PDC; furthermore they show that polyuridine RNAs lack TLR7 activity if uridines are bound to adenosine and not guanosine, suggesting that not the mere uridine content of RNA per se, but rather binding of uridine to guanosine determines the TLR7 ligand activity of double stranded RNA.

Example 7

Evidence that Some RNA Hairpins Containing G·U Base Pairs Act as Selective TLR8 Agonists (A) PBMC were isolated from Buffy coats and stimulated with the RNAs shown in (B) in complex with Poly-1-Arginine. After 20 h IFN-a, IL-12 p70 and IL-6 were measured in the supernatants by cytokine Elisa. R2151 CGCGCGCGCAGAAGCGUGCGC (SEQ ID NO: 30) and R2152 CGCGUGCGCAGAAGCGCGCGC (SEQ ID NO: 31) are examples for selective TLR8 agonists. These data show, that also cells expressing TLR8, as for example human monocytes, can selectively be activated by RNA oligos that contain a single uridine in a G·U wobble base pair. In this case, RNA sequences that showed selective TLR8 activation the U involved in the G·U base pair was preferentially flanked by G on either side.

Example 8

In Cells that Express Both Functional TLR7 and TLR8 RNAs Containing G·U Wobble Base Pairs Retain TLR7 Selective Activity THP-1 cells were matured with 300ng/ml PMA for 4 h in a 10cm dish, then harvested, washed with PBS twice and plated at 100.000 cells/well of a 96 well Plate. PMA activated THP-1 cells express TLR8, and upon stimulation with IFN-g (100 U/ml) for 8 h also upregulate functional TLR7 (adapted from Gantier et al. TLR7 is involved in sequence-specific sensing of single-stranded RNAs in human macrophages. J Immunol (2008) vol. 180 (4) pp. 2117-24). (A) THP-1 cells were stimulated with the small molecule agonists R848 (TLR7/8 agonist) CI087 (TLR7 agonist), or RNAs R2153, R2116 (TLR7 agonists) R2127 (inert), and 9.2s (TLR7/8 agonist). After 20 h TNF-a was measured in the culture supernatant by ELISA. (B) Knockdown of TLR7 using 3 different lentiviral shRNA constructs in PMA/IFN-g treated THP-1 cells represses TLR7 but not TLR8 mRNA. THP-1 cells were infected with shRNA lentiviruses targeting TLR7 and with control viruses. Stable lines were obtained and maintained by antibiotic selection with Puromycin (2μg/ml) for 10 days Lentiviral vectors without (empty) or with nonsense shRNA (scrambled) were used as negative controls. THP-1 cells were treated as described in A and harvested after 8h treatment with IFN-g. RNA was extracted and TLR7/8 expression normalized to GAPDH levels was analyzed by SYBR Green real-time RT-PCR. (C) THP-1 cells treated as in described in (B) were stimulated with small molecule agonists (R848, CI087 and CI075[TLR8 agonist]), or the indicated RNAs in complex with Poly-1-Arginine (R2161CGCCUGGGCAGAAGCCCGGGC) (SEQ ID NO: 33). After 20 h TNF-a was measured in the culture supernatant by ELISA. Data shown are representative of 2 (A) or 3 (B, C) independent experiments. These data show that the strictly TLR7 selective activation via RNA oligos containing an immune stimulatory G·U base pairs is maintained even when functional TLR8 is expressed within the same cell.

REFERENCES

1. Uematsu S, Akira S: Toll-Like receptors (TLRs) and their ligands. *Handb Exp Pharmacol* 2008:1-20.
2. Alexopoulou L, Holt A C, Medzhitov R, Flavell R A: Recognition of double-stranded RNA and activation of NF-kappaB by Toll-like receptor 3. *Nature* 2001, 413: 732-738.
3. Krug A, Luker G D, Barchet W, Leib D A, Akira S, Colonna M: Herpes simplex virus type 1 activates murine natural interferon-producing cells through toll-like receptor 9. *Blood* 2004, 103:1433-1437.
4. Lund J, Sato A, Akira S, Medzhitov R, Iwasaki A: Toll-like receptor 9-mediated recognition of Herpes simplex virus-2 by plasmacytoid dendritic cells. *J Exp Med* 2003, 198:513-520.
5. Lund J M, Alexopoulou L, Sato A, Karow M, Adams N C, Gale N R, Iwasaki A, Flavell R A: Recognition of single-stranded RNA viruses by Toll-like receptor 7. *Proc Natl Acad Sci USA* 2004, 101:5598-5603.
6. Diebold S S, Kaisho T, Hemmi H, Akira S, Reis e Sousa C: Innate antiviral responses by means of TLR7-mediated recognition of single-stranded RNA. *Science* 2004, 303: 1529-1531.
7. Heil F, Hemmi H, Hochrein H, Ampenberger F, Kirschning C, Akira S, Lipford G, Wagner H, Bauer S: Species-specific recognition of single-stranded RNA via toll-like receptor 7 and 8. *Science* 2004, 303:1526-1529.
8. Hemmi H, Takeuchi O, Kawai T, Kaisho T, Sato S, Sanjo H, Matsumoto M, Hoshino K, Wagner H, Takeda K, et al.: A Toll-like receptor recognizes bacterial DNA. *Nature* 2000, 408:740-745.
9. Hornung V, Rothenfusser S, Britsch S, Krug A, Jahrsdorfer B, Giese T, Endres S, Hartmann G: Quantitative expression of toll-like receptor 1-10 mRNA in cellular subsets of human peripheral blood mononuclear cells and sensitivity to CpG oligodeoxynucleotides. *J Immunol* 2002, 168:4531-4537.
10. Kadowaki N, Ho S, Antonenko S, Malefyt R W, Kastelein R A, Bazan F, Liu Y J: Subsets of human dendritic cell precursors express different toll-like receptors and respond to different microbial antigens. *J Exp Med* 2001, 194:863-869.
11. Jurk M, Heil F, Vollmer J, Schetter C, Krieg A M, Wagner H, Lipford G, Bauer S: Human TLR7 or TLR8 independently confer responsiveness to the antiviral compound R-848. *Nat Immunol* 2002, 3:499.
12. Ma Y, Li J, Chiu I, Wang Y, Sloane J A, Lu J, Kosaras B, Sidman R L, Volpe J J, Vartanian T: Toll-like receptor 8 functions as a negative regulator of neurite outgrowth and inducer of neuronal apoptosis. *J Cell Biol* 2006, 175:209-215.
13. Gorden K B, Gorski K S, Gibson S J, Kedl R M, Kieper W C, Qiu X, Tomai M A, Alkan S S, Vasilakos J P: Synthetic TLR agonists reveal functional differences between human TLR7 and TLR8. *J Immunol* 2005, 174: 1259-1268.
14. Heil F, Ahmad-Nejad P, Hemmi H, Hochrein H, Ampenberger F, Gellert T, Dietrich H, Lipford G, Takeda K, Akira S, et al.: The Toll-like receptor 7 (TLR7)-specific stimulus loxoribine uncovers a strong relationship within the TLR7, 8 and 9 subfamily. *Eur J Immunol* 2003, 33:2987-2997.
15. Lee J, Chuang T H, Redecke V, She L, Pitha P M, Carson D A, Raz E, Cottam H B: Molecular basis for the immunostimulatory activity of guanine nucleoside analogs: activation of Toll-like receptor 7. *Proc Natl Acad Sci USA* 2003, 100:6646-6651.
16. Wagstaff A J, Perry C M: Topical imiquimod: a review of its use in the management of anogenital warts, actinic keratoses, basal cell carcinoma and other skin lesions. *Drugs* 2007, 67:2187-2210.
17. Barchet W, Krug A, Cella M, Newby C, Fischer J A, Dzionek A, Pekosz A, Colonna M: Dendritic cells respond to influenza virus through TLR7- and PKR-independent pathways. *Eur J Immunol* 2005, 35:236-242.
18. Diebold S S, Massacrier C, Akira S, Paturel C, Morel Y, Reis e Sousa C: Nucleic acid agonists for Toll-like receptor 7 are defined by the presence of uridine ribonucleotides. *Eur J Immunol* 2006, 36:3256-3267.
19. Eberle F, Giessler K, Deck C, Heeg K, Peter M, Richert C, Dalpke A H: Modifications in Small Interfering RNA That Separate Immunostimulation from RNA Interference. *J Immunol* 2008, 180:3229-3237.
20. Forsbach A, Nemorin J G, Montino C, Muller C, Samulowitz U, Vicari A P, Jurk M, Mutwiri G K, Krieg A M, Lipford G B, et al.: Identification of RNA Sequence Motifs Stimulating Sequence-Specific TLR8-Dependent Immune Responses. *J Immunol* 2008, 180:3729-3738.
21. Hornung V, Guenthner-Biller M, Bourquin C, Ablasser A, Schlee M, Uematsu S, Noronha A, Manoharan M, Akira S, de Fougerolles A, et al.: Sequence-specific potent induction of IFN-alpha by short interfering RNA in plasmacytoid dendritic cells through TLR7. *Nat Med* 2005, 11:263-270.
22. Judge A D, Sood V, Shaw J R, Fang D, McClintock K, MacLachlan I: Sequence-dependent stimulation of the mammalian innate immune response by synthetic siRNA. *Nat Biotechnol* 2005, 23:457-462.
23. Scheel B, Teufel R, Probst J, Carralot J P, Geginat J, Radsak M, Jarrossay D, Wagner H, Jung G, Rammensee H G, et al.: Toll-like receptor-dependent activation of several human blood cell types by protamine-condensed mRNA. *Eur J Immunol* 2005, 35:1557-1566.
24. Sioud M: Single-stranded small interfering RNA are more immunostimulatory than their double-stranded counterparts: a central role for 2'-hydroxyl uridines in immune responses. *Eur J Immunol* 2006, 36:1222-1230.
25. Mathews D H, Turner D H: Prediction of RNA secondary structure by free energy minimization. *Curr Opin Struct Biol* 2006, 16:270-278.
26. Masquida B, Westhof E: On the wobble GoU and related pairs. *RNA* 2000, 6:9-15.
27. Varani G, McClain W H: The G×U wobble base pair. A fundamental building block of RNA structure crucial to RNA function in diverse biological systems. *EMBO Rep* 2000, 1:18-23.
28. Xu D, Landon T, Greenbaum N L, Fenley M O: The electrostatic characteristics of G·U wobble base pairs. *Nucleic Acids Res* 2007, 35:3836-3847.
29. Diebold S S, Montoya M, Unger H, Alexopoulou L, Roy P, Haswell L E, Al-Shamkhani A, Flavell R, Borrow P, Reis e Sousa C: Viral infection switches non-plasmacytoid dendritic cells into high interferon producers. *Nature* 2003, 424:324-328.
30. Gitlin L, Barchet W, Gilfillan S, Cella M, Beutler B, Flavell R A, Diamond M S, Colonna M: Essential role of mda-5 in type I IFN responses to polyriboinosinic:polyribocytidylic acid and encephalomyocarditis picornavirus. *Proc Natl Acad Sci USA* 2006, 103:8459-8464.
31. Bekeredjian-Ding I, Roth S I, Gilles S, Giese T, Ablasser A, Hornung V, Endres S, Hartmann G: T cell-independent, TLR-induced IL-12p70 production in primary human monocytes. *J Immunol* 2006, 176:7438-7446.
32. Bekeredjian-Ding I B, Wagner M, Hornung V, Giese T, Schnurr M, Endres S, Hartmann G: Plasmacytoid dendritic cells control TLR7 sensitivity of naive B cells via type I IFN. *J Immunol* 2005, 174:4043-4050.
33. Barrat F J, Meeker T, Gregorio J, Chan J H, Uematsu S, Akira S, Chang B, Duramad O, Coffman R L: Nucleic acids of mammalian origin can act as endogenous ligands for Toll-like receptors and may promote systemic lupus erythematosus. *J Exp Med* 2005, 202:1131-1139.
34. Krieg A M, Vollmer J: Toll-like receptors 7, 8, and 9: linking innate immunity to autoimmunity. *Immunol Rev* 2007, 220:251-269.
35. Lau C M, Broughton C, Tabor A S, Akira S, Flavell R A, Mamula M J, Christensen S R, Shlomchik M J, Viglianti G A, Rifkin I R, et al.: RNA-associated autoantigens activate B cells by combined B cell antigen receptor/Toll-like receptor 7 engagement. *J Exp Med* 2005, 202:1171-1177.
36. Hattermann K, Picard S, Borgeat M, Leclerc P, Pouliot M, Borgeat P: The Toll-like receptor 7/8-ligand resiquimod (R-848) primes human neutrophils for leukotriene B4, prostaglandin E2 and platelet-activating factor biosynthesis. *FASEB J* 2007, 21:1575-1585.
37. Chuang T H, Ulevitch R J: Cloning and characterization of a sub-family of human toll-like receptors: hTLR7, hTLR8 and hTLR9. *Eur Cytokine Netw* 2000, 11:372-378.
38. Palecanda A, Kobzik L: Receptors for unopsonized particles: the role of alveolar macrophage scavenger receptors. *Curr Mol Med* 2001, 1:589-595.

The invention claimed is:

1. A single-stranded or double-stranded specifically TLR7-activating RNA poly/oligonucleotide, wherein the specifically TLR7-activating RNA poly/oligonucleotide does not activate TLR8,
   wherein the specifically TLR7-activating RNA poly/oligonucleotide comprises:
   (i) a stem loop structure as set forth by Formula I or II comprising a double-stranded section:

$5'X_n$ G/C GGG G/C $V_m N_o W_m$ C/G CUC C/G $Y_n 3'$  (Formula I)

$5'X_n$ C/G CUC C/G $V_m N_o W_m$ G/C GGG G/C $Y_n 3'$  (Formula II)

wherein X is any base that forms a Watson-Crick base pair with Y, V is any base that forms a Watson-Crick base pair with W, and N is any base in the loop of the stem-loop structure; wherein $0 \le n \le 10$, $0 \le m < 10$ and $2 \le o \le 12$; provided that the total length of the stem loop structure set forth by Formula I or II is 15-45 bases;
   or
   (ii) a double stranded section, wherein one strand of the double-stranded section comprises a structure set forth by Formula III and the other strand of the double-stranded section comprises a structure set forth by Formula IV:

$5'X_n$ G/C GGG G/C $V_m$ 3'  (Formula III)

$5'W_m$ C/G CUC C/G $Y_n$ 3'  (Formula IV)

wherein X is any base that forms a Watson-Crick base pair with Y, V is any base that forms a Watson-Crick base pair with W; wherein $0 \le n \le 10$, $0 \le m \le 10$, provided that the total length of each strand defined by Formulae III and IV is 5-45 bases.

2. The specifically TLR7-activating RNA poly/oligonucleotide of claim 1, which does not contain AU base pairs, and which does not contain an unpaired U base.

3. The specifically TLR7-activating RNA poly/oligonucleotide of claim 1, wherein the RNA poly/oligonucleotide exhibits selective TLR7 activity without complexation.

4. The specifically TLR7-activating RNA poly/oligonucleotide of claim 1 comprising at least one unpaired U base.

5. A pharmaceutical composition comprising at least one specifically TLR7-activating RNA poly/oligonucleotide of claim 1.

6. The pharmaceutical composition of claim 5, further comprising at least one agent selected from the group consisting of an immunostimulatory agent, an anti-viral agent, an anti-bacterial agent, an anti-tumor agent, IFN-α, and IFN-β.

7. A method of inducing type I IFN production comprising administering the specifically TLR7-activating poly/oligonucleotide of claim 1 to a subject in need thereof.

8. A method of treating a tumor, a chronic HBV infection, or a chronic HCV infection, comprising administering the specifically TLR7-activating poly/oligonucleotide of claim 1 to a subject in need thereof.

9. The method of claim 8, further comprising administering at least one agent selected from the group consisting of an anti-viral agent and an anti-tumor agent to the subject.

10. The pharmaceutical composition of claim 5, further comprising exogenous G nucleoside.

11. The pharmaceutical composition of claim 5, further comprising a prophylactic and/or a therapeutic agent for treating an infection, a tumor, and/or an immune disorder.

12. An in vitro method for inducing type I IFN production in a cell, comprising:
   (a) mixing at least one specifically TLR7-activating RNA poly/oligonucleotide of claim 1 with a complexation agent; and
   (b) contacting the cell with the mixture of (a), wherein the cell expresses TLR7 and is capable of producing type I IFN upon TLR7 activation.

13. An in vitro method for inducing type I IFN production in a cell, comprising the steps of:
  contacting the cell with at least one specifically TLR7-activating RNA poly/oligonucleotide of claim 1,
  wherein the cell expresses TLR7 and is capable of producing an anti-viral response upon TLR7 activation.

14. A method for preparing the single-stranded specifically TLR7-activating RNA poly/oligonucleotide of claim 1 comprising:
  (a) identifying a RNA poly/oligonucleotide sequence that self-hybridizes to form the at least one double-stranded section comprising the stem-loop structure set forth by Formula I or II, and
  (b) producing an RNA poly/oligonucleotide having the nucleotide sequence identified in (a).

15. The specifically TLR7-activating RNA poly/oligonucleotide of claim 1, wherein the double-stranded section comprises 4-8 G:C base pairs.

\* \* \* \* \*